United States Patent
Oshima et al.

(10) Patent No.: US 9,511,030 B2
(45) Date of Patent: *Dec. 6, 2016

(54) CONTROLLED RELEASE PARTICLES

(75) Inventors: Junji Oshima, Osaka (JP); Takayuki Sugiyama, Osaka (JP)

(73) Assignee: OSAKA GAS CHEMICALS CO., LTD., Osaka-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/003,271

(22) PCT Filed: Mar. 8, 2012

(86) PCT No.: PCT/JP2012/055968
§ 371 (c)(1),
(2), (4) Date: Sep. 5, 2013

(87) PCT Pub. No.: WO2012/124598
PCT Pub. Date: Sep. 20, 2012

(65) Prior Publication Data
US 2013/0337073 A1    Dec. 19, 2013

(30) Foreign Application Priority Data

Mar. 11, 2011  (JP) ................................ 2011-054628
Feb. 23, 2012  (JP) ................................ 2012-037885

(51) Int. Cl.
*A61K 9/50* (2006.01)
*A01N 25/28* (2006.01)

(52) U.S. Cl.
CPC ............ *A61K 9/5026* (2013.01); *A01N 25/28* (2013.01)

(58) Field of Classification Search
None
See application file for complete search history.

(56) References Cited

U.S. PATENT DOCUMENTS

| | | | |
|---|---|---|---|
| 4,656,205 | A | 4/1987 | Walker et al. |
| 4,923,894 | A | 5/1990 | Kanda et al. |
| 5,073,276 | A | 12/1991 | Newlove et al. |
| 5,225,279 | A * | 7/1993 | Redlich et al. ........... 428/402.22 |
| 5,972,363 | A | 10/1999 | Clikeman et al. |
| 6,365,066 | B1 | 4/2002 | Podszun et al. |
| 6,471,975 | B1 | 10/2002 | Banovetz et al. |
| 7,354,596 | B1 | 4/2008 | Banovetz et al. |
| 2005/0282011 | A1 | 12/2005 | Yokoyama et al. |
| 2007/0215000 | A1 | 9/2007 | Reybuck et al. |
| 2012/0172334 | A1* | 7/2012 | Oshima ........................ 514/63 |
| 2013/0337072 | A1* | 12/2013 | Oshima .................. A01N 25/28 424/497 |
| 2015/0010635 | A1* | 1/2015 | Oshima .................. A01N 47/12 424/489 |
| 2015/0141549 | A1* | 5/2015 | Oshima .................. A01N 25/10 523/456 |

FOREIGN PATENT DOCUMENTS

| | | |
|---|---|---|
| CA | 2082892 A1 | 5/1993 |
| CA | 2321440 A1 | 8/1999 |
| EP | 1 230 855 A1 | 8/2002 |
| JP | 59-145265 A | 8/1984 |
| JP | 60-132642 A | 7/1985 |
| JP | 61-86941 A | 5/1986 |
| JP | 61-236702 A | 10/1986 |
| JP | 5-212271 A | 8/1993 |
| JP | 7-053835 A | 2/1995 |
| JP | 10-324601 A | 12/1998 |
| JP | 2008-218154 A | 8/2000 |
| JP | 2001-502733 A | 2/2001 |
| JP | 2001-247409 A | 9/2001 |
| JP | 2002-503679 A | 2/2002 |
| JP | 2002-513038 A | 5/2002 |
| JP | 2002-513039 A | 5/2002 |
| JP | 2004-331625 A | 11/2004 |
| JP | 2006-035210 A | 2/2006 |
| JP | 2007-246527 A | 9/2007 |
| JP | 2008-074809 A | 4/2008 |
| JP | 2008-239561 A | 10/2008 |
| JP | 2008-239562 A | 10/2008 |
| WO | WO 01/37660 A1 | 5/2001 |

OTHER PUBLICATIONS

Notification Concerning Transmittal of International Preliminary Report on Patentability (Form PCT/ISA/326), Notification of Transmittal of Translation of the International Preliminary Report on Patentability (Forms of PCT/IB/373 and PCT/IB/338) and the Written Opinion of the International Searching Authority (Form PCT/ISA/237) issued on Aug. 6, 2012 in the corresponding International Application No. PCT/JP2012/055968. (14 Pages).
International Search Report (PCT/ISA/210) mailed on Jun. 12, 2012, by the Japanese Patent Office as the International Searching Authority for International Application No. PCT/JP2012/055968.
Written Opinion (PCT/ISA/237) mailed on Jun. 12, 2012, by the Japanese Patent Office as the International Searching Authority for International Application No. PCT/JP2012/055968.
Iconomopoulou, S.M., et al., "Incorporation of Low Molecular Weight Biocides Into Polystyrene-Divinyl Benzene Beads With Controlled Release Characteristics," Journal of Controlled Release, 2005, vol. 102, No. 1, pp. 223-233.

(Continued)

*Primary Examiner* — Bethany Barham
*Assistant Examiner* — Ping Cao
(74) *Attorney, Agent, or Firm* — Buchanan, Ingersoll & Rooney PC

(57) ABSTRACT

A controlled release particle includes a core formed by suspension polymerization of a core ingredient component containing an antibiotic compound and a first polymerizable vinyl monomer, and containing a first polymer of the first polymerizable vinyl monomer and the antibiotic compound present in the first polymer; and a shell formed by suspension polymerization of a second polymerizable vinyl monomer having affinity with water of the same or higher than that of the first polymerizable vinyl monomer, containing a second polymer obtained from the second polymerizable vinyl monomer, and covering the core.

1 Claim, 1 Drawing Sheet

(56) References Cited

OTHER PUBLICATIONS

Vyas, S.P., et al.,"Formulation of Sustained Release Nitrofurantoin by Interfacial Copolymerization Method," Indian Drugs, 1980, vol. 18, No. 1 pp. 8-10.

Arun, A., et al., "In Vitro Drug Release Studies of 2-Hydroxyethyl Acrylate or 2-Hydroxypropyl Methacrylate-4-[1E,4E)-5[4-Acryloyloxy)Phenyl]-3OXOPENTA-1,4-Dienyl} Phenyl Acrylate Copolymer Beads," Journal of Biomedical Materials Research Part B: Applied Biomaterials, 2005, vol. 73B, No. 2, pp. 291-300.

Croswell, Roger W. et al., "Suspension Polymerization for Preparation of Timed-Release Dosage Forms," Journal of Pharmaceutical Sciences, 1974, vol. 63, No. 3, pp. 440-442.

Masayoshi, Okubo, et al., "Production of Composite Polymer Particles Encapsulating Hinokitiol," Japan Chemical Society Lecture Preliminary Drafts, 2001, vol. 79, No. 1, p. 425.

Kassem, Aly A., "Formulation and Evaluation of Controlled Dissolution Phenobarbitone Macremolecular Products Employing In-Situ Suspension Polymerization With Methylmethacrylate," Egyptian Journal of Pharmaceutical Sciences, 1978, vol. 19, No. 1-4, pp. 143-162.

Notice of Reasons for Refusal issued on Feb. 21, 2014, by the Japanese Patent Office in Japanese Patent Application No. 2010-201604, and an partial English translation of the Notice. (7 pages).

Kosmetik, et al. "Perlpolymerisate, Eine Neue Perorale Darreichungsform Und Ihre Beeinflussung Durch Arzneistoffe," Praparative Pharmazie, 1970, vol. 6, No. 9/10, pp. 149-154.

\* cited by examiner

TEM photograph of Example 4
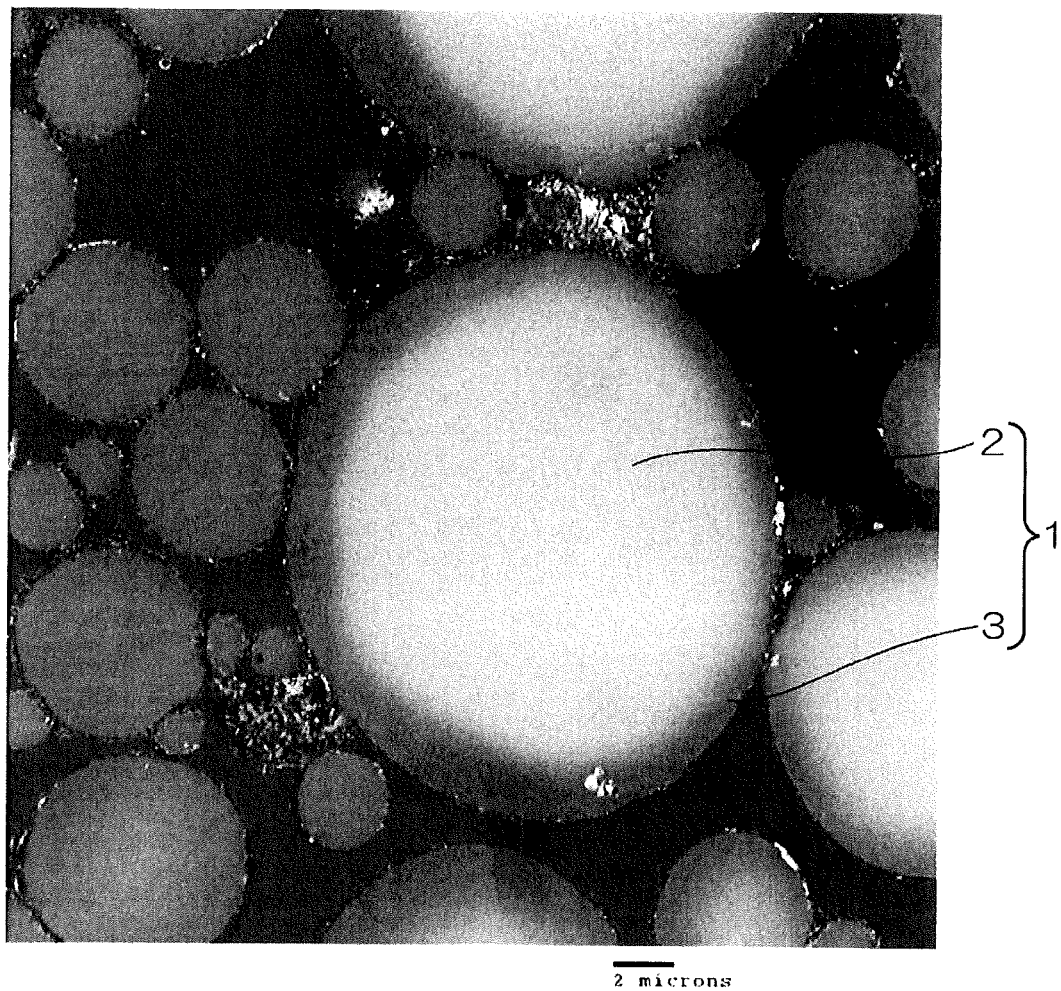
2 microns

CONTROLLED RELEASE PARTICLES

TECHNICAL FIELD

The present invention relates to controlled release particles, in particular, to controlled release particles that allow controlled-release of an antibiotic compound.

BACKGROUND ART

It is known that micro-encapsulation of antibiotic compounds such as a sterilizer, an antiseptic, and a fungicide allows controlled-release of the antibiotic compound to ensure lasting effects.

For example, a microbial growth inhibitor-containing microcapsule (for example, see Patent Document 1 below) has been proposed: the microbial growth inhibitor-containing microcapsule is obtained by blending and dispersing an oil phase including a microbial growth inhibitor and a polyisocyanate component, and an aqueous phase including an active hydrogen group-containing component, and allowing interfacial polymerization.

CITATION LIST

Patent Document

Patent Document 1: Japanese Unexamined Patent Publication No. 2001-247409

SUMMARY OF THE INVENTION

Problem to be Solved by the Invention

However, there are disadvantages in the above-described Patent Document 1 in that the microbial growth inhibitor-containing microcapsule described in Patent Document 1 has insufficient controlled release properties.

An object of the present invention is to provide controlled release particles excellent in controlled release properties.

Means for Solving the Problem

The present inventors made an energetic study on the controlled release particles of the above object, and found out that controlled release particles have excellent controlled release properties by including a core containing an antibiotic compound present in the first polymer and a shell composed of a second polymer, and as a result of further advancing the study, accomplished the present invention.

That is, a controlled release particle of the present invention includes,
(1) a core formed by suspension polymerization of a core ingredient component containing an antibiotic compound and a first polymerizable vinyl monomer, and containing a first polymer of the first polymerizable vinyl monomer and the antibiotic compound present in the first polymer; and a shell formed by suspension polymerization of a second polymerizable vinyl monomer having affinity with water of the same or higher than that of the first polymerizable vinyl monomer, containing a second polymer obtained from the second polymerizable vinyl monomer, and covering the core.

Effect of the Invention

A controlled release particle of the present invention includes a core containing a first polymer obtained from a first polymerizable vinyl monomer, and an antibiotic compound present in a matrix composed of the first polymer; and a shell composed of a second polymer and is formed so as to cover the core. Therefore, by suppressing the releasing speed of the antibiotic compound, the controlled release particle of the present invention has excellent controlled release properties, and exhibits excellent lasting effects.

BRIEF DESCRIPTION OF THE DRAWINGS

FIG. 1 shows an image-processed TEM photograph of controlled release particles of Example 4.

EMBODIMENT OF THE INVENTION

As shown in the TEM photograph of FIG. 1, the controlled release particle (1) of the present invention includes a core (2), and a shell (3) that covers the core (2).

The core (2) is generally spherical, and contains a first polymer and an antibiotic compound.

The shell (3) is formed into a membrane that covers the surface of the core (2), and contains a second polymer. The shell (3) is formed along the periphery of the core (2), and has a comparatively smooth surface.

In the controlled release particle (1) of the present invention, the core (2) is formed by suspension polymerization of a core ingredient component containing the antibiotic compound and a first polymerizable vinyl monomer, and the shell (3) is formed by suspension polymerization of a second polymerizable vinyl monomer.

The antibiotic compound has, for example, at least two functional moieties that are capable of interacting with the polymer of the first polymerizable vinyl monomer.

Examples of such functional moieties include polar functional groups such as a carbonyl group, a nitro group, an amino group, a cyano group, a phosphate group, a carboxyl group, and an ether group; polar bonds containing a polar group such as a carboxylate bond, a phosphate bond, a urea bond, and a carbon-halogen bond; and conjugated cyclic portions such as a benzene ring, and further a conjugated heterocyclic ring such as a triazine ring, an imidazole ring, and an isothiazoline ring.

The antibiotic compound has a molecular weight of, for example, 200 to 600, preferably 200 to 500.

When the antibiotic compound has a molecular weight exceeding the above-described range, miscibility of the antibiotic compound with the first polymer may be reduced. On the other hand, when the antibiotic compound has a molecular weight below the above-described range, there is a case where the antibiotic compound remains in the aqueous phase during suspension polymerization, and after the suspension polymerization, the antibiotic compound separates out, solidifying the first suspension liquid.

The antibiotic compound has a melting point of, for example, 100° C. or less, preferably 90° C. or less, and more preferably 80° C. or less. When the antibiotic compound has a melting point exceeding the above-described range, there may be a case where the antibiotic compound is not easily encapsulated in the core and separates outside the core, and even if the antibiotic compound is encapsulated in the core, controlled-release of the antibiotic compound to the outside the core may not be allowed.

To be specific, the antibiotic compound is selected from a sterilizer, an antibacterial agent, an antiseptic, an antialgae, a fungicide, an insecticide, a herbicide, an attractant, a repellent, a rodenticide, etc. having antibiotic activities such as, for example, sterilizing, antibacterial, antiseptic, antialgae, antifungal, and insecticidal activity. Examples of these compounds having antibiotic activity include sterilizing antiseptic antialgae fungicides such as an iodine compound, a triazole compound, a carbamoyl imidazole compound, a dithiol compound, an isothiazoline compound, a nitro alcohol compound, and p-hydroxybenzoate ester; and termite control agents (termite killers) such as a pyrethroid compound, a neonicotinoid compound, an organic chlorine compound, an organic phosphorus compound, a carbamate compound, an alkoxyamine compound, and an oxadiazon compound.

Examples of iodine compounds include 3-iodo-2-propynylbutylcarbamate (IPBC), 1-[[(3-iodo-2-propynyl)oxy]methoxy]-4-methoxybenzene, and 3-bromo-2,3-diiodo-2-propenyl ethyl carbonate.

Examples of triazole compounds include 1-[2-(2,4-dichlorophenyl)-4-n-propyl-1,3-dioxolane-2-ylmethyl]-1H-1,2,4-triazole (propiconazole), and bis(4-fluorophenyl)methyl (1H-1,2,4-triazole-1-ylmethylsliane) (also called: flusilazole, 1-[[bis(4-fluorophenyl) methylsilyl]methyl]-1H-1,2,4-triazole).

Examples of carbamoyl imidazole compounds include N-propyl-N-[2-(2,4,6-trichloro-phenoxy)ethyl]imidazole-1-carboxamide (prochloraz).

Examples of dithiol compounds include 4,5-dichloro-1,2-dithiol-3-one.

Examples of isothiazoline compounds include 2-n-octyl-4-isothiazoline-3-one (OIT), 5,6-dichloro-2-n-octyl-4-isothiazoline-3-one (DCOIT), and 5-chloro-2-methyl-4-isothiazoline-3-one (Cl-MIT).

Examples of nitro alcohol compounds include 2,2-dibromo-2-nitro-1-ethanol (DBNE).

Examples of p-hydroxybenzoate esters include butyl p-hydroxybenzoate and propyl p-hydroxybenzoate.

Examples of pyrethroid compounds include pyrethrin obtained from pyrethrum, cinerin, and jasmoline; and also include allethrin, bifenthrin, acrinathrin, α-cypermethrin, tralomethrin, cyfluthrin ((RS)-α-cyano-4-fluoro-3-phenoxybenzyl=(1RS,3RS)-(1RS,3RS)-3-(2,2-dichlorovinyl)-2,2-methylcyclopropane carboxylate), cyphenothrin, prallethrin, ethofenprox, silafluofen, and fenvalerate derived therefrom.

Examples of neonicotinoid compounds include (E)-$N^1$-[(6-chloro-3-pyridyl)methyl]-$N^2$-cyano-$N^1$-methylacetamidine (acetamiprid).

Examples of organic chlorine compounds include Kelthane.

Examples of organic phosphorus compounds include phoxim, pyridaphenthion, fenitrothion, tetrachlorvinphos, dichlofenthion, and propetamphos.

Examples of carbamate compounds include fenobucarb and propoxur.

Examples of alkoxyamine compound include 3-lauryloxypropylamine.

Examples of oxadiazon compounds include indoxacarb.

Examples of insecticides include pyriproxyfen.

Examples of herbicides include pyraclonil, pendimethalin, and indanofan.

Examples of repellents include Deet.

The antibiotic compound is substantially hydrophobic, and, to be specific, has a quite low water solubility at room temperature (20 to 30° C., to be more specific, 25° C.), to more be specific, for example, a solubility at room temperature of on a mass basis, 1 part by mass/100 parts by mass of water (10000 ppm) or less, preferably 0.5 parts by mass/100 parts by mass of water (5000 ppm) or less, and more preferably 0.1 parts by mass/100 parts by mass of water (1000 ppm) or less; and on a volume basis, for example, 1 g/100 mL of water or less, preferably 0.5 g/100 mL of water or less, and more preferably 0.1 g/100 mL of water or less.

When the antibiotic compound has a water solubility exceeding the above-described range, at the time of suspension polymerization of a core ingredient component containing the first polymerizable vinyl monomer, the antibiotic compound easily leaks out to the outside (that is, aqueous phase) of the core, and after the polymerization, the antibiotic compound dissolved in the aqueous phase separates out, and therefore formation of the core containing the antibiotic compound may become difficult.

These antibiotic compounds can be used alone or in combination of two or more.

The above-described antibiotic compound may contain, for example, in the production processes, impurities having a melting point of outside the above-described range at an appropriate proportion. To be specific, a mixture of isomer I (melting point: 57° C.), isomer II (melting point: 74° C.), and isomer III (melting point: 66° C.) of cyfluthrin contains, for example, an impurity of isomer IV (melting point 102° C.).

The first polymerizable vinyl monomer is, for example, a monomer having at least one polymerizable carbon-carbon double bond in its molecule.

To be specific, examples of the first polymerizable vinyl monomer include a (meth)acrylate monomer, a (meth)acrylic acid monomer, an aromatic vinyl monomer, a vinyl ester monomer, a maleate monomer, a vinyl halide monomer, and a nitrogen-containing vinyl monomer.

Examples of (meth)acrylate monomers include methacrylates and/acrylates, to be specific, (meth) acrylic acid alkyl ester having an alkyl moiety of a straight chain or branched aliphatic group with 1 to 20 carbon atoms including methyl (meth)acrylate, ethyl (meth)acrylate, propyl (meth)acrylate, isopropyl (meth)acrylate, butyl (meth)acrylate, isobutyl (meth)acrylate, tert-butyl (meth)acrylate, hexyl (meth)acrylate, octyl (meth)acrylate, nonyl (meth)acrylate, isononyl (meth)acrylate, decyl (meth)acrylate, dodecyl (meth)acrylate, hexadecyl (meth)acrylate, and octadecyl (meth)acrylate; and (meth) acrylic acid cycloalkyl ester having an alkyl moiety of a cyclic aliphatic group having 3 to 20 carbon atoms including cyclopentyl (meth)acrylate, cyclohexyl (meth)acrylate, and cycloheptyl (meth)acrylate.

Preferably, (meth) acrylic acid alkyl ester having an alkyl moiety of a straight chain or branched aliphatic group with 1 to 6 carbon atoms (preferably, having 1 to 3 carbon atoms or having 4 to 6 carbon atoms) is used.

Examples of (meth) acrylic acid ester monomers also include hydroxyl group-containing (meth) acrylic acid alkyl ester in which the hydrogen atoms in the alkyl moiety are replaced with hydroxyl groups in the above-described monomer, and which has a hydroxyalkyl moiety with 2 to 10 carbon atoms, to be specific, 2-hydroxyethyl (meth)acrylate, 3-hydroxypropyl (meth)acrylate, 4-hydroxybutyl (meth)acrylate, and 6-hydroxyhexyl (meth)acrylate.

Preferably, hydroxyl group-containing (meth) acrylic acid alkyl ester having a hydroxyalkyl moiety having an acrylic moiety with 2 to 6 carbon atoms (preferably, with 2 to 3 carbon atoms) is used.

Examples of (meth) acrylic acid monomers include methacrylic acid and acrylic acid.

Examples of aromatic vinyl monomers include styrene, 4-chlorostyrene, p-methyl styrene, o-methyl styrene, and α-methyl styrene.

Examples of vinyl ester monomers include vinyl acetate and vinyl propionate.

Examples of maleate monomers include dimethyl maleate, diethyl maleate, and dibutyl maleate.

Examples of vinyl halide monomers include vinyl chloride and vinyl fluoride. Examples of vinyl halide monomer also include vinylidene halide monomers, to be specific, vinylidene chloride and vinylidene fluoride.

Examples of nitrogen-containing vinyl monomers include (meth)acrylonitrile, N-phenylmaleimide, and vinylpyridine.

The first polymerizable vinyl monomer is substantially hydrophobic, and to be specific, has a significantly low water solubility at room temperature, to be more specific, a solubility at room temperature of, for example, 10 parts by mass/100 parts by mass of water or less, preferably 8 parts by mass/100 parts by mass of water or less.

Of the above-described first polymerizable vinyl monomers, for example, an antibiotic compound-miscible monomer (hereinafter sometimes simply referred to as a miscible monomer) that is highly miscible with the above-described antibiotic compound and is capable of dissolving (being miscible with) the antibiotic compound is selected.

These miscible monomers can be used alone or in combination of two or more.

As the miscible monomer, preferably, a (meth)acrylate monomer and a (meth)acrylic acid monomer are used in combination.

To be specific, methyl methacrylate (MMA) and methacrylic acid (MA) are used in combination, or isobutyl methacrylate (IBMA) and methacrylic acid (MA) are used in combination.

When a (meth)acrylate monomer and a (meth)acrylic acid monomer are used in combination, the mixing ratio of the (meth)acrylic acid monomer relative to 100 parts by mass of the miscible monomer is, for example, below 30 parts by mass, preferably 20 parts by mass or less, and, for example, 1 part by mass or more, preferably 3 parts by mass or more.

A combination of the antibiotic compound and the miscible monomer is selected so that, preferably, the first polymer, i.e., a polymer of the first polymerizable vinyl monomer, and the antibiotic compound are miscible at a polymerization temperature (heating temperature) to be described later.

The first polymerizable vinyl monomer can contain a crosslinkable monomer as the miscible monomer.

The crosslinkable monomer is blended as necessary to adjust controlled release properties of the controlled release particles, and examples of the crosslinkable monomer include mono or polyethylene glycol di(meth)acrylate such as ethylene glycol di(meth)acrylate and diethylene glycol di(meth)acrylate; alkane diol di(meth)acrylate such as 1,3-propanediol di(meth)acrylate, 1,4-butanediol di(meth)acrylate, and 1,5-pentanediol di(meth)acrylate; alkane polyol poly(meth)acrylate such as trimethylolpropane tri(meth)acrylate and pentaerythritol tetra(meth)acrylate; allyl monomers such as allyl (meth) methacrylate, and triallyl (iso) cyanurate; and divinyl monomers such as divinylbenzene. Preferably, mono or polyethylene glycol di(meth)acrylate is used.

As the crosslinkable monomer, a monomer having a molecule structure that is similar to that of the miscible monomer excluding the crosslinkable monomer is selected to ensure miscibility of the antibiotic compound and the monomer mixture (first polymerizable vinyl monomer) including the crosslinkable monomer; to be specific, when the miscible monomer excluding the crosslinkable monomer contains a (meth) acrylic acid ester monomer, preferably, mono or polyethylene glycol di(meth)acrylate is selected as the crosslinkable monomer.

The mixing ratio of the crosslinkable monomer relative to 100 parts by mass of the miscible monomer excluding the crosslinkable monomer is, for example, 1 to 100 parts by mass, preferably 5 to 90 parts by mass, and more preferably 10 to 80 parts by mass.

In the core ingredient component, as the antibiotic compound and the first polymerizable vinyl monomer, a combination of the following is selected: an antibiotic compound having a polar term $\delta_{p,compound}$ of, for example, 2 to 8$[(J/cm^3)^{1/2}]$ and a hydrogen bonding term $\delta_{h,compound}$ of, for example, 5.0 to 9.5$[(J/cm^3)^{1/2}]$ of the solubility parameter $\delta$ defined by Hansen and calculated by van Krevelen and Hoftyzer method; and a first polymerizable vinyl monomer that produces a first polymer having a polar term $\delta_{p,first\ polymer}$ of 4 to 7$[(J/cm^3)^{1/2}]$ and a hydrogen bonding term $\delta_{h,first\ polymer}$ of 8 to 10$[(J/cm^3)^{1/2}]$ of the solubility parameter $\delta$.

The indexes "compound", "first polymer", and "second polymer" in each term $\delta$ ($\delta_p$ and $\delta_h$) represent the antibiotic compound, the first polymer, and the second polymer, respectively.

The polar term $\delta_p$ and the hydrogen bonding term $\delta_h$ of the solubility parameter $\delta$ defined by Hansen and calculated by van Krevelen and Hoftyzer method depend on the types and the number of the atomic group (including chemical bond or substituent), to be specific, are represented by following formulas (1) and (2), respectively.

[Mathematical Formula 1]

$$\delta_p = \frac{\sqrt{\Sigma F_{pi}^2}}{V} \quad (1)$$

(where $F_p$ represents polar component of the molar attraction function, and V represents molar volume)

$$\delta_h = \sqrt{\frac{\Sigma E_{hi}}{V}} \quad (2)$$

(where $E_h$ represents contribution of the hydrogen bonding forces to the cohesive energy, and V represents molar volume.)

Values of the above-described $F_p$, $E_h$, and V are described in "Properties of Polymers" (3rd Edition, Chapter 7, pp 189 to 225, written by van Krevelen, ELSEVIER, issued in 2003) by atomic group.

$F_p$ and $E_h$ of substituent —I, >Si<, =N— and ≡C— are not described in the above-described document, but calculated by professor Hideki Yamamoto of Kansai University by the following method.

First, an example of the calculation method for $F_p$ of substituent —I is given.

Ten compounds containing substituent —I described in "Hansen Solubility Parameters, A User's Handbook" (written by Charles Hansen, pp 347 to 483 (Appendix), CRC Press, issued in 2007) are randomly selected, and the left side of the above-described formula (1) is substituted by the value of compound $\delta_p$ described in the above-described document. Furthermore, the right side of the above-described formula (2) is substituted by values of V of all atomic groups of the ten compounds selected as described above, and $F_p$ of the atomic group excluding the substituent —I, while $F_p$ of the substituent —I in the right side is rendered unknown.

Then, the equation in which $\delta_p$ of the compound and V of all atomic groups are known, and $F_p$ of the atomic group excluding the substituent is known, and $F_p$ of substituent —I is unknown is solved, and the average of the solution $(F_p)$ of the ten compound as $F_p$ of substituent —I is calculated.

$F_p$ of the substituent >Si<, =N—, and ≡C— is also calculated in the above-described manner.

$E_h$ of the substituent —I, >Si<, =N—, and ≡C— can also be calculated in the above-described manner.

The above-described calculation process is recorded in a computer as a program, and optimized.

$F_p$ and $E_h$ of the substituent —I, >Si<, =N—, and ≡C— calculated as described above are noted below.

—I $F_p$: 0 $(J^{1/2} \cdot cm^{3/2} \cdot mol^{-1})$
$E_h$: 0 $(J \cdot mol^{-1})$
>Si< $F_p$: 0 $(J^{1/2} \cdot cm^{3/2} \cdot mol^{-1})$
$E_h$: 0 $(J \cdot mol^{-1})$
=N— $F_p$: 800 $(J^{1/2} \cdot cm^{3/2} \cdot mol^{-1})$
$E_h$: 3000 $(J \cdot mol^{-1})$
≡C— $F_p$: 0 $(J^{1/2} \cdot cm^{3/2} \cdot mol^{-1})$
$E_h$: 0 $(J \cdot mol^{-1})$ Next, as an example of first polymers, polymethyl methacrylate (PMMA), i.e., a polymer of methyl methacrylate, is given as an example, and a polar term $\delta_{p,PMMA}$ and a hydrogen bonding term $\delta_{h,PMMA}$ of the solubility parameter $\delta$ of polymethyl methacrylate is calculated.

1. Polar Term $\delta_p$ and Hydrogen Bonding Term $\delta_h$ of Homopolymer
(1) Structural Formula of Polymethyl Methacrylate Polymethyl methacrylate is represented by formula (3) below.

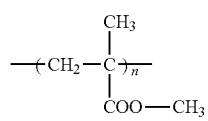

(3)

(where n represents degree of polymerization)
(2) Polar Term $\delta_{p,PMMA}$ $F_p$ and V of atomic groups in the monomer unit (—CH$_2$—C(CH$_3$)COOCH$_3$—) of the above-described formula (3) are shown below.

—CH$_3$ $F_p$: 0 $(J^{1/2} \cdot cm^{3/2} \cdot mol^{-1})$
V: 33.5 $(cm^3 \cdot mol)$
—CH$_2$— $F_p$: 0 $(J^{1/2} \cdot cm^{3/2} \cdot mol^{-1})$
V: 16.1 $(cm^3 \cdot mol)$
>C< $F_p$: 0 $(J^{1/2} \cdot cm^{3/2} \cdot mol^{-1})$
V: −19.2 $(cm^3 \cdot mol)$
—COO— $F_p$: 490 $(J^{1/2} \cdot cm^{3/2} \cdot mol^{-1})$
V: 18 $(cm^3 \cdot mol)$ Therefore, polar term $\delta_{p,monomer\ unit}$ of the monomer unit is calculated, as shown in formula (4) below, to be 5.98$[(J/cm^3)^{1/2}]$.

$$\delta_p = \frac{\sqrt{\Sigma F_{pi}^2}}{V} \quad (4)$$

$$= \frac{\sqrt{0^2 + 0^2 + 0^2 + 490^2}}{2 \times 33.5 + 16.1 + (-19.2) + 18}$$

$$= 5.98 \left[ (J/cm^3)^{1/2} \right]$$

Then, the polar term $\delta_{p,monomer\ unit}$ of the above-described monomer unit is rendered the polar term $\delta_{p,PMMA}$ of polymethyl methacrylate, having a repeating structure of the monomer unit.

(3) Hydrogen Bonding Term $\delta_{h,PMMA}$ $E_h$ of the atomic groups in the monomer unit (—CH$_2$—C(CH$_3$)COOCH$_3$—) of the above-described formula (3) is shown below.

—CH$_3$ $E_h$: 0 $(J \cdot mol^{-1})$
—CH$_2$— $E_h$: 0 $(J \cdot mol^{-1})$
>C< $E_h$: 0 $(J \cdot mol^{-1})$
—COO— $E_h$: 7000 $(J \cdot mol^{-1})$ Therefore, the hydrogen bonding term $\delta_{h,monomer\ unit}$ of the monomer unit is calculated, as shown in formula (5) below, to be 9.25$[(J/cm^3)^{1/2}]$.

$$\delta_h = \sqrt{\frac{\Sigma E_{hi}}{V}} \quad (5)$$

$$= \sqrt{\frac{0 + 0 + 0 + 7000}{2 \times 33.5 + 16.1 + (-19.2) + 18}}$$

$$= 9.25 \left[ (J/cm^3)^{1/2} \right]$$

Then, the above-described hydrogen bonding term $\delta_{h,first\ polymer}$ of the monomer unit is rendered the hydrogen bonding term $\delta_{h,PMMA}$ of polymethyl methacrylate, having a repeating structure of the monomer unit.

2. Polar Term $\delta_p$ and Hydrogen Bonding Term $\delta_h$ of Copolymer

Next, polar term $\delta_p$ and hydrogen bonding term $\delta_h$ of a copolymer is calculated.

By multiplying the polar term $\delta_{p,monomer\ unit}$ of monomer units by the mass ratio of the monomer, and by adding these, the polar term $\delta_{p,copolymer}$ of the solubility parameter $\delta$ of the copolymer is calculated. Also, by multiplying the hydrogen bonding term $\delta_{h,monomer\ unit}$ of the monomer units by the mass ratio of the monomer, and adding these, the hydrogen bonding term $\delta_{h,copolymer}$ of the solubility parameter $\delta$ of the copolymer is calculated.

As an example of the copolymer, a polymethyl methacrylate-polymethacrylic acid-ethylene glycol dimethacrylate copolymer (PMMA-MA-EGDMA), i.e., a copolymer of a monomer containing methyl methacrylate, methacrylic acid, and ethylene glycol dimethacrylate in a mass ratio of 75:12.5:12.5 (corresponds to the mass ratio of Example 1 to be described later), is used, and its polar term $\delta_{p,PMMA-PMA-EGDMA}$ and the hydrogen bonding term $\delta_{h,PMMA-PMA-EGDMA}$ of the solubility parameter $\delta$ are calculated.

(1) Polar Term $\delta_{p,PMMA-PMA-EGDMA}$

The polar term $\delta_{p,MMA\ unit}$ of the monomer unit of methyl methacrylate is, as calculated above, 5.98$[(J/cm^3)^{1/2}]$.

The polar term $\delta_{p,MA\ unit}$ of the monomer unit of methacrylic acid calculated as described above is, 7.36$[(J/cm^3)^{1/2}]$.

The polar term $\delta_{p,EGDMA}$ of the monomer unit of ethylene glycol dimethacrylate is calculated in the same manner as above, and determined to be 5.37$[(J/cm^3)^{1/2}]$.

The polar term $\delta_{p,PMMA-PMA-EGDMA}$ of the copolymer is calculated as shown in formula (6) below.

$$\delta_{p,PMMA-PMA-EGDMA} = (75/100)\delta_{p,MMA\ unit} + (12.5/100)\delta_{p,MA\ unit} + \quad (6)$$

$$(12.5/100)\delta_{p,EGDMA\ unit}$$

$$= (75/100) \times 5.98 + (12.5/100) \times$$

$$7.36 + (12.5/100) \times 5.37$$

$$= 6.07 \left[ (J/cm^3)^{1/2} \right]$$

(2) Hydrogen Bonding Term $\delta_{h,PMMA\text{-}PMA\text{-}EGDMA}$

The hydrogen bonding term $\delta_{h,MMA\ Unit}$ of the monomer unit of methyl methacrylate is $9.25[(J/cm^3)^{1/2}]$.

The hydrogen bonding term $\delta_{h,MA\ unit}$ of the monomer unit of methacrylic acid is $9.25[(J/cm^3)^{1/2}]$.

The hydrogen bonding term $\delta_{h,EGDMA}$ of the monomer unit of ethylene glycol dimethacrylate is $10.42[(J/cm^3)^{1/2}]$.

The hydrogen bonding term $\delta_{h,PMMA\text{-}PMA\text{-}EGDMA}$ of the copolymer is calculated as shown in formula (7) below.

$$\delta_{h,PMMA\text{-}PMA\text{-}EGDMA} = (75/100)\delta_{h,MMA\ unit} + (12.5/100)\delta_{h,MA\ unit} + \quad (7)$$
$$(12.5/100)\delta_{h,EGDMA\ unit}$$
$$= (75/100) \times 9.25 + (12.5) \times 10.25 + (12.5) \times 10.42$$
$$= 9.52[(J/cm^3)^{1/2}]$$

The polar term $\delta_{p,first\ polymer}$ of the solubility parameter $\delta$ of the first polymer is preferably 4.25 to $6.5[(J/cm^3)^{1/2}]$, and the hydrogen bonding term $\delta_{h,first\ polymer}$ of the solubility parameter $\delta$ of the first polymer is preferably 8.25 to $10[(J/cm^3)^{1/2}]$.

When the polar term $\delta_{p,first\ polymer}$ and/or the hydrogen bonding term $\delta_{h,first\ polymer}$ of the first polymer are below the above-described range, the first polymer becomes excessively hydrophobic, and sufficient miscibility with the antibiotic compound may not be obtained, and even if miscibility was obtained, the antibiotic compound leaks to the outside of the core during the suspension polymerization, making synthesis of controlled release particles in which the antibiotic compound is sufficiently encapsulated difficult.

On the other hand, when the polar term $\delta_{p,first\ polymer}$ and/or the hydrogen bonding term $\delta_{h,first\ polymer}$ of the first polymer exceeds the above-described range, there may be a case where hydrophilicity of the first polymer becomes excessively high and sufficient miscibility with the antibiotic compound cannot be obtained, and even if miscibility could be obtained, interfacial free energy with the aqueous phase in the suspension polymerization is lowered, and antibiotic compound leaks to the outside of the core during the suspension polymerization, making synthesis of the core in which the antibiotic compound is sufficiently encapsulated difficult.

3. Polar Term $\delta_{p,compound}$ and Hydrogen Bonding Term $\delta_{h,compound}$ of Solubility $\delta$ of Antibiotic Compound The polar term $\delta_{p,compound}$ and the hydrogen bonding term $\delta_{h,compound}$ of the solubility $\delta$ of the antibiotic compound are also calculated in the same manner as that of the above-described monomer unit.

Table 1 shows the results of the calculated polar term $\delta_{p,\ compound}$ and hydrogen bonding term $\delta_{h,compound}$ of antibiotic compounds, i.e., IPBC, OIT, cyfluthrin, propiconazole, prochloraz, and flusilazole.

TABLE 1

| Antibiotic Compound | Polar Term $\delta_{p,compound}$ $[J/cm^3]^{1/2}$ | Hydrogen Bonding Term $\delta_{h,compound}$ $[J/cm^3]^{1/2}$ |
|---|---|---|
| IPBC | 3.23 | 7.83 |
| OIT | 5.47 | 5.87 |
| Cyfluthrin | 3.46 | 6.09 |
| Propiconazole | 6.55 | 9.44 |
| Prochloraz | 6.87 | 8.85 |
| Flusilazole | 5.95 | 6.85 |

The polar term $\delta_{p,\ compound}$ of solubility parameter $\delta$ of the antibiotic compound is preferably 3 to $7[(J/cm^3)^{1/2}]$ and the hydrogen bonding term $\delta_{h,\ compound}$ is preferably 5.8 to 9.5 $[(J/cm^3)^{1/2}]$.

When the polar term $\delta_{p,compound}$ and/or the hydrogen bonding term $\delta_{h,compound}$ of the antibiotic compound is below the above-described range, there may be a case where hydrophobicity of the antibiotic compound becomes excessively high and sufficient miscibility with the first polymer may not be obtained.

On the other hand, when the polar term $\delta_{p,compound}$ and/or the hydrogen bonding term $\delta_{h,compound}$ of the antibiotic compound exceed the above-described range, there may be a case where hydrophilicity of the antibiotic compound becomes excessively high and the antibiotic compound easily leaks to the outside of the core, making synthesis of the core in which the antibiotic compound is sufficiently encapsulated difficult.

4. Difference in Polar Term $\delta_p$ ($\Delta\delta_{p1}$) and Difference in Hydrogen Bonding Term $\delta_h$ ($\Delta\delta_{h1}$) of Solubility Parameter In the present invention, the value of $\Delta\delta_{p1}(=\delta_{p,first\ polymer}-\delta_{p,compound})$ deducting the polar term $\delta_{p,compound}$ of the antibiotic compound from the polar term $\delta_{p,first\ polymer}$ of the solubility parameter $\delta$ of the first polymer is, for example, $-2.5$ to $3.0[(J/cm^3)^{1/2}]$, preferably $-1.1$ to $2.7[(J/cm^3)^{1/2}]$, more preferably 0 to $2.6[(J/cm^3)^{1/2}]$.

The value of $\Delta\delta_{h1}(=\delta_{h,first\ polymer}-\delta_{h,compound})$ deducting the hydrogen bonding term $\delta_{h,compound}$ of the antibiotic compound from the hydrogen bonding term $\delta_{h,first\ polymer}$ of the first polymer is, for example, $-1.1$ to $4.5[(J/cm^3)^{1/2}]$, preferably 0 to $4.2[(J/cm^3)^{1/2}]$.

When $\Delta\delta_{p1}$ and $\Delta\delta_{h1}$ are within the above-described range, excellent miscibility of the antibiotic compound and the first polymer can be ensured, ensuring excellent controlled release properties.

When the polar term $\delta_{p,compound}$ and the hydrogen bonding term $\delta_{h,compound}$ of the antibiotic compound are within the above-described range, and the polar term $\delta_{p,first\ polymer}$ and the hydrogen bonding term $\delta_{h,first\ polymer}$ of the first polymer are within the above-described range, the antibiotic compound is defined as being miscible with the first polymer without leaking from the core during suspension polymerization.

The ratio of the antibiotic compound relative to the first polymerizable vinyl monomer is, on a mass basis (that is, parts by mass of the antibiotic compound/parts by mass of the first polymerizable vinyl monomer), for example, 10/90 to 90/10 (that is, 0.11 to 9.0), preferably 10/90 to 70/30 (that is, 0.11 to 2.33).

The second polymerizable vinyl monomer has affinity (that is, hydrophilicity) with water that is higher than that of the first polymerizable vinyl monomer (to be specific, miscible monomer), and to be specific, examples thereof include those monomers that are the same types as those of the above-described first polymerizable vinyl monomers, and that have high affinity with water.

Examples of the second polymerizable vinyl monomer that may be used is, preferably, (meth)acrylic acid ester monomers, more preferably, hydroxyl group-containing (meth)acrylic acid alkyl ester and (meth)acrylic acid alkyl ester.

To be more specific, as the second polymerizable vinyl monomer, hydroxyl group-containing (meth)acrylic acid alkyl ester (to be specific, hydroxyl group-containing (meth) acrylic acid alkyl ester having a hydroxyalkyl moiety with 2 to 3 carbon atoms) is used singly, (meth)acrylic acid alkyl ester (to be specific, (meth)acrylic acid alkyl ester having an alkyl moiety with 1 to 3 carbon atoms) is used singly, or they are used in combination.

When the hydroxyl group-containing (meth)acrylic acid alkyl ester having a hydroxyalkyl moiety with 2 to 3 carbon atoms is used singly as the second polymerizable vinyl monomer, for example, a combination of (meth)acrylic acid alkyl ester having 4 to 6 carbon atoms and (meth)acrylic acid monomer, preferably, a combination of (meth)acrylic acid alkyl ester having 4 carbon atoms and methacrylic acid is used as the first polymerizable vinyl monomer.

When (meth)acrylic acid alkyl ester having an alkyl moiety with 1 to 3 carbon atoms is used singly as the second polymerizable vinyl monomer, for example, a combination of (meth)acrylic acid alkyl ester having 4 to 6 carbon atoms and a (meth)acrylic acid monomer, preferably, a combination of (meth)acrylic acid alkyl ester having 4 carbon atoms and methacrylic acid is selected as the first polymerizable vinyl monomer.

When a combination of hydroxyl group-containing (meth)acrylic acid alkyl ester having a hydroxyalkyl moiety with 2 to 3 carbon atoms and (meth)acrylic acid alkyl ester having an alkyl moiety with 1 to 3 carbon atoms are used in combination as the second polymerizable vinyl monomer, for example, a combination of (meth)acrylic acid alkyl ester having 4 to 6 carbon atoms and (meth) an acrylic acid ester monomer, preferably, a combination of (meth)acrylic acid alkyl ester having 4 carbon atoms and methacrylic acid is selected as the first polymerizable vinyl monomer.

The polar term $\delta_{p,second\ polymer}$ of the second polymer, i.e., the polymer of the above-described second polymerizable vinyl monomer, is, for example, 5.0 to 9.0$[(J/cm^3)^{1/2}]$, preferably, 6.5 to 8.0$[(J/cm^3)^{1/2}]$, and the hydrogen bonding term $\delta_{h,second\ polymer}$ of the solubility parameter $\delta$ of the second polymer is, for example, 8.0 to 20.0$[(J/cm^3)^{1/2}]$, preferably, 12.0 to 18.0$[(J/cm^3)^{1/2}]$.

When the polar term $\delta_{p,second\ polymer}$ and/or the hydrogen bonding term $\delta_{h,second\ polymer}$ of the second polymer exceed the above-described range, the second polymer becomes excessively hydrophilic, and the second polymer forming the shell dissolves in water or absorbs water to swell, which makes it difficult to maintain the shape of the shell.

On the other hand, when the polar term $\delta_{p,second\ polymer}$ and/or the hydrogen bonding term $\delta_{h,second\ polymer}$ of the second polymer are below the above-described range, there may be a case where the second polymer is insufficiently hydrophilic, the shell cannot achieve the barrier layer functions to be described later, and is miscible with the antibiotic compound to cause the antibiotic compound to leak to the outside of the shell.

The value of $\Delta\delta_{p2}(=\delta_{p,second\ polymer}-\delta_{p,first\ polymer})$ deducting the polar term $\delta_{p,first\ polymer}$ of the first polymer from the polar term $\delta_{p,second\ polymer}$ of the second polymer of the solubility parameter $\delta$ is, for example, $-1.5[(J/cm^3)^{1/2}]$ or more, preferably 0.0$[(J/cm^3)^{1/2}]$ or more, more preferably 2.0$[(J/cm^3)^{1/2}]$ or more, and usually 10.0$[(J/cm^3)^{1/2}]$ or less.

The value $\Delta\delta_{h2}(=\delta_{h,second\ polymer}-\delta_{h,first\ polymer})$ deducting the hydrogen bonding term $\delta_{h,first\ polymer}$ of the first polymer from the hydrogen bonding term $\delta_{h,second\ polymer}$ of the second polymer is, for example, $-1.0[(J/cm^3)^{1/2}]$ or more, preferably 0.0$[(J/cm^3)^{1/2}]$ or more, more preferably 2.0$[(J/cm^3)^{1/2}]$ or more, and usually 20.0$[(J/cm^3)^{1/2}]$ or less.

When $\Delta\delta_{p2}$ and/or $\Delta\delta_{h2}$ are below the above-described lower limit value, there may be a case where affinity with water of the second polymer cannot be made higher than that of the first polymer, and thus functions of the barrier layer to be described later cannot be achieved, and as a result, and the second polymer is miscible with the antibiotic compound to cause the antibiotic compound to leak to the outside of the shell.

On the other hand, when $\Delta\delta_{p2}$ and/or $\Delta\delta_{h2}$ exceed the above-described upper limit value, there may be a case where affinity with water of the second polymer becomes excessive (excessively hydrophilic), and the second polymer dissolves in water or absorbs water to swell, which makes it difficult to maintain the shape of the shell.

When $\Delta\delta_{p2}$ and/or $\Delta\delta_{h2}$ are more than the above-described lower limit value, affinity with water (hydrophilic/hydrophilicity) of the second polymer becomes higher than the first polymer. In other words, the second polymerizable vinyl monomer is defined as having higher affinity (hydrophilicity) with water than that of the first polymerizable vinyl monomer.

To obtain controlled release particles of the present invention, first, suspension polymerization of the core ingredient component containing the antibiotic compound and the first polymerizable vinyl monomer is carried out.

To be specific, the core ingredient component is prepared as a hydrophobic solution containing the antibiotic compound and the first polymerizable vinyl monomer.

To prepare the hydrophobic solution, for example, the antibiotic compound is dissolved in the first polymerizable vinyl monomer (or miscible in the first polymerizable vinyl monomer) in the absence of a solvent.

With the hydrophobic solution, preferably, an initiator is blended.

Examples of the initiator include oil-soluble radical polymerization initiators, and examples of the radical polymerization initiator include organic peroxides such as dilauroyl peroxide (10 hours half-life temperature $T_{1/2}$: 61.6° C.), 1,1,3,3-tetramethylbutylperoxy-2-ethylhexanoate (10 hours half-life temperature $T_{1/2}$: 65.3° C.), t-hexylperoxy-2-ethylhexanoate (10 hours half-life temperature $T_{1/2}$: 69.4° C.), diisopropylperoxydicarbonate (10 hours half-life temperature $T_{1/2}$: 40.5° C.), and benzoylperoxide (10 hours half-life temperature $T_{1/2}$: 73.6° C.); and azo compounds such as 2,2'-azobisisobutyronitrile (10 hours half-life temperature $T_{1/2}$: 60° C.), 2,2'-azobis(2,4-dimethylvaleronitrile) (10 hours half-life temperature $T_{1/2}$: 51° C.), and 2,2'-azobis(2-methylbutyronitrile)(10 hours half-life temperature $T_{112}$: 67° C.). Preferably, organic peroxide is used.

The mixing ratio of the initiator relative to 100 parts by mass of the first polymerizable vinyl monomer is, for example, 0.01 parts by mass or more, preferably 0.1 parts by mass or more, more preferably 1 part by mass or more, particularly preferably 2.0 parts by mass or more, and usually, for example, 10 parts by mass or less.

When the mixing ratio of the initiator is the above-described lower limit value or more, the conversion rate of the second polymerizable vinyl monomer in suspension polymerization to be described next can be increased.

The initiator is blended at the same time with the blending of the above-described antibiotic compound and the first polymerizable vinyl monomer, or before or after the blending. Preferably, the initiator is dissolved, when the antibiotic compound is dissolved in the first polymerizable vinyl monomer simultaneously.

Preparation of the hydrophobic solution may be performed, for example, at normal temperature, or as necessary, can be performed by heating to 30 to 100° C. Preferably, in view of suppressing thermal decomposition of the initiator, the hydrophobic solution is prepared at normal temperature without heating.

Next, the hydrophobic solution is suspended (aqueously dispersed) in water.

That is, the hydrophobic solution and water are blended, and the mixture is stirred homogeneously, thereby allowing the hydrophobic solution to be suspended. A first water suspension liquid of the hydrophobic solution is obtained in this manner.

Conditions for the suspension are not particularly limited. For example, the suspension may be performed at normal temperature, or can be performed by heating to 30 to 100° C. Preferably, in view of suppressing thermal decomposition of the initiator, the suspension is performed without heating.

The mixing ratio of water relative to 100 parts by mass of the hydrophobic solution is, for example, 10 to 1000 parts by mass, preferably 50 to 500 parts by mass.

When the hydrophobic solution is suspended, for example, a dispersing agent is blended.

Examples of dispersing agents include water-soluble polymers such as polyvinyl alcohol (PVA, including partially saponified polyvinyl alcohol), polyvinyl pyrrolidone, gelatin, gum arabic, hydroxyethyl cellulose, hydroxypropyl cellulose, carboxymethyl cellulose, cationized starch, polyacrylic acid and its sodium salt, and styrene maleic acid copolymer and its sodium salt; and inorganic dispersing agents such as tribasic calcium phosphate, colloidal silica, montmorillonite, magnesium carbonate, aluminum hydroxide, and zinc white.

Of the dispersing agents, preferably, inorganic dispersing agent, and more preferably, tribasic calcium phosphate is used. When the tribasic calcium phosphate is used, and when the obtained controlled release particles are formulated into powder formulation (described later) or granular formulation (described later), re-dispersiveness of the powder formulation or granular formulation is improved, and occurrence of caking can be prevented.

The mixing ratio of the dispersing agent relative to 100 parts by mass of the hydrophobic solution is, for example, 0.1 to 20 parts by mass, preferably 0.1 to 15 parts by mass.

When the hydrophobic solution is suspended, a surfactant can be used in combination along with the above-described dispersing agent.

The surfactant is blended to effectively prevent aggregation of the core in the suspension polymerization. Examples of the surfactant include anionic surfactants such as sodium dodecylbenzenesulfonate (DBN), sodium lauryl sulfate, sodium di-2-ethylhexyl sulfosuccinate, sodium dodecyl diphenyl ether disulphonate, sodium nonyl diphenyl ether sulfonate, sodium polyoxyethylene alkyl ether sulfonate, ammonium polyoxyethylene alkyl ether phosphate, naphthalenesulfonic acid formaldehyde condensate sodium salt, and sodium dialkylsulfosuccinic acid; and non-ionic surfactants such as polyoxyethylene lauryl ether, polyoxyethylenenonylphenylether, polyoxyethylene monostearate, polyoxyethylene sorbitan monooleate, polyoxyethylene polyoxypropylene block copolymer, and polyoxyethylene phosphate. Preferably, non-ionic surfactants are used.

The mixing ratio of the surfactant relative to 100 parts by mass of the hydrophobic solution is, for example, 0.0001 to 1.0 parts by mass, preferably 0.001 to 0.1 parts by mass.

These dispersing agents and surfactants can be blended, for example, before or after the blending of the hydrophobic solution with water. Preferably, these dispersing agents and surfactants are blended in water before being blended with the hydrophobic solution. An aqueous solution of the dispersing agent and the surfactant are prepared in this manner.

For the above-described suspension of the hydrophobic solution, for example, dispersers such as a homomixer, Disper, an ultrasonic homogenizer, a pressurized homogenizer, Milder, and a porous membrane injection disperser are used.

Preferably, Homo Mixer is used, and its number of revolution is, for example, 200 to 20000 rpm, preferably 1500 to 15000 rpm.

The suspension time (stirring time) of the first suspension liquid is, for example, 20 minutes or less, preferably for 3 to 10 minutes.

Then, by increasing the temperature of the first suspension liquid, suspension polymerization of the core ingredient component is performed (first step).

In suspension polymerization, the first polymerizable vinyl monomer is allowed to react (to be specific, vinyl polymerization) while stirring the first suspension liquid so as to maintain the suspension state of the first suspension liquid, thereby producing a polymer (first polymer) of the first polymerizable vinyl monomer. Furthermore, because the ingredient, the first polymerizable vinyl monomer, is in the hydrophobic phase (oil phase), it is called in situ polymerization.

To perform suspension polymerization, first, the temperature of the first suspension liquid is increased so that the temperature of the first suspension liquid is higher than the 10 hours half-life temperature $T_{1/2}$ of the initiator by, for example, more than 0° C. to 30° C. or less, preferably, more than 5° C. to 20° C. or less. The first suspension liquid can also be heated to the temperature of the 10 hours half-life temperature $T_{1/2}$ of the initiator.

In the first suspension liquid whose temperature is increasing, for example, under an atmosphere of inert gas such as nitrogen, the initiator undergoes thermal decomposition at a certain temperature, causing suspension polymerization to start.

To be specific, the polymerization temperature in the first step is, for example, 30 to 100° C., preferably 40 to 80° C., more preferably 50 to 75° C.

The pressure at the time of suspension polymerization is not particularly limited, and suspension polymerization is carried out at normal pressure. Or, the suspension polymerization is carried out at high pressure. Preferably, the suspension polymerization is carried out at normal pressure.

The polymerization time in the first step is, for example, 1 hour or more, preferably 3 hours or more, more preferably 4 hours or more, and usually 10 hours or less.

The above-described suspension polymerization allows the antibiotic compound to be present in the matrix composed of the first polymer.

In this manner, the core containing the first polymer and the antibiotic compound is formed.

Thereafter, the second polymerizable vinyl monomer is subjected to suspension polymerization.

To subject the second polymerizable vinyl monomer to suspension polymerization, first, for example, the first suspension liquid after the reaction is cooled.

To be specific, the suspension liquid after reaction is cooled, for example, by allowing the suspension liquid after reaction to stand to cool, or by water.

The cooling temperature of the first suspension liquid is a temperature which allows suppression of thermal decomposition of the initiator remaining in the core, to be specific, for example, 50° C. or less, preferably 40° C. or less, more preferably normal temperature or less, and usually 5° C. or more.

Or, the first suspension liquid after reaction can also be used, for example, without cooling, in the next suspension polymerization of the second polymerizable vinyl monomer.

Then, the second polymerizable vinyl monomer is blended with the first suspension liquid, and the mixture is allowed to react.

The second polymerizable vinyl monomer is prepared as an emulsified liquid containing the second polymerizable vinyl monomer.

The emulsified liquid is prepared by emulsifying the second polymerizable vinyl monomer in water in the presence of an emulsifier.

Examples of the emulsifier include those surfactants described above, and preferably, anionic surfactants are used.

The mixing ratio of the emulsifier relative to 100 parts by mass of the emulsified liquid is, for example, 0.0001 to 1.0 parts by mass, preferably 0.001 to 0.1 parts by mass.

The emulsifier can be blended, for example, before or after the blending of the second polymerizable vinyl monomer with water. Preferably, the emulsifier is blended with water before blending with the second polymerizable vinyl monomer. An aqueous solution of the emulsifier is prepared in this manner.

The mixing ratio of the second polymerizable vinyl monomer relative to 100 parts by mass of water is, for example, 10 to 1000 parts by mass, preferably 50 to 500 parts by mass.

For emulsification of the second polymerizable vinyl monomer, for example, the above-described disperser is used. Preferably, Homo Mixer is used, and its number of revolution is higher than the number of revolution in the suspension of the first suspension liquid, to be specific, for example, 200 to 20000 rpm, preferably 1500 to 15000 rpm.

With the emulsified liquid, a silane coupling agent can be blended.

A silane coupling agent can be blended.

The silane coupling agent is, for example, an alkoxysilyl compound having at least a vinyl group or a (meth) acryloyl group, to be specific, for example, a vinyl group-containing alkoxysilyl compound such as vinyltrimethoxysilane and vinyltriethoxysilane; and (meth) acryloyl-group containing alkoxysilyl compounds such as methacryloxypropylmethyldimethoxysilane, 3-methacryloxypropyltrimethoxysilane, 3-methacryloxypropylmethyldiethoxysilane, 3-methacryloxypropyltriethoxysilane, and 3-acryloxypropyltrimethoxysilane.

The mixing ratio of the silane coupling agent relative to 100 parts by mass of the second polymerizable vinyl monomer is, for example, 0.01 to 10 parts by mass, preferably 0.1 to 1 parts by mass.

The preparation of the emulsified liquid can be carried out, for example, at normal temperature, or as necessary, for example, while heating to 30 to 100° C. Preferably, in view of suppressing the self-polymerization of the second polymerizable vinyl monomer, the emulsified liquid is prepared at normal temperature without heating.

Emulsification time is, for example, 20 minutes or less, preferably for 3 to 20 minutes.

Thereafter, the prepared emulsified liquid is blended with the first suspension liquid, and the mixture is stirred to prepare a second suspension liquid.

For the preparation of the above-described second suspension liquid, the above-described disperser is used. Preferably, Homo Mixer is used, and its number of revolution is, for example, 200 to 20000 rpm, preferably 1500 to 15000 rpm.

The suspension time (stirring time) of the second suspension liquid is, in view of sufficiently allowing the second polymerizable vinyl monomer to adsorb on the surface of the core, for example, 0.1 hour or more, preferably 1 hour or more, more preferably 2 hours or more, and usually 10 hours or less.

In preparation of the second suspension liquid, the second polymerizable vinyl monomer in the emulsified liquid is attached to (absorbed by) the core composed of the first polymer.

Then, by increasing the temperature of the second suspension liquid, suspension polymerization of the second polymerizable vinyl monomer is performed (second step).

To perform suspension polymerization of the second suspension liquid, first, the temperature of the second suspension liquid is increased so that the temperature of the second suspension liquid is higher than the 10 hours half-life temperature $T_{1/2}$ of the initiator by, for example, more than 0° C. to 30° C. or less, preferably more than 5° C. to 20° C. or less. The second suspension liquid can also be heated to the temperature of the 10 hours half-life temperature $T_{1/2}$ of the initiator.

In the second suspension liquid during temperature increase, for example, under an atmosphere of inert gas such as nitrogen, the remaining initiator undergoes thermal decomposition at a certain temperature, causing suspension polymerization to start.

The polymerization temperature of the second step is the same as that of the polymerization temperature of the first step.

The pressure at the time of the suspension polymerization of the second suspension liquid is not particularly limited, and is a constant pressure. Or, the suspension polymerization can be carried out at high pressure. Preferably, the suspension polymerization is carried out at normal pressure.

The polymerization time of the second step is, for example, 0.1 hour or more, preferably 1 hour or more, more preferably 2 hours or more, and usually 10 hours or less.

In suspension polymerization, the second polymerizable vinyl monomer is allowed to react while stirring the second suspension liquid so as to maintain the suspension state of the second suspension liquid, thereby producing a polymer (second polymer) of the second polymerizable vinyl monomer.

The suspension polymerization of the second polymerizable vinyl monomer allows covering of the core, and forming of the shell composed of the second polymer.

Thereafter, the second suspension liquid after the reaction is cooled.

To be specific, the second suspension liquid is cooled, for example, by allowing the second suspension liquid after reaction to stand to cool, or by water. The cooling temperature is, for example, room temperature (20 to 30° C., to be more specific, 25° C.).

After the cooling, the antibiotic compound is present in the first polymer in the core.

That is, when the antibiotic compound is solid at room temperature, in the matrix composed of the first polymer in the core, the miscible state is frozen, and the homogenous state is kept.

Or, after cooling, when the antibiotic compound is liquid at room temperature, as shown in FIG. 1, the antibiotic compound is miscible with (dissolved in) the first polymer in the core (2).

By the above-described production method, as shown in FIG. 1, the suspension liquid including controlled release particles (1) including the core (2) and the shell (3) can be obtained.

The particle size of the controlled release particles is not particularly limited, and the average particle size (median size) is, for example, 1 µm to 1 mm, preferably 2 to 100 µm.

The core has a particle size, i.e., an average particle size (median size) of for example, 1 to 1000 µm, preferably 2 to 50 µm.

The shell has a thickness, i.e., the maximum thickness of, for example, 0.01 to 500 µm, preferably 0.05 to 50 µm.

The particle size of the core and the thickness of the shell are calculated from, for example, a TEM photograph of the obtained controlled release particles. The particle size of the core can be also measured by taking out the particles composed only of the core from the suspension liquid after the first step, and measuring the particles composed only of the core by a laser diffraction scattering particle size distribution analyzer.

In this manner, a suspension liquid in which controlled release particles are suspended can be obtained, the controlled release particles including the core containing the antibiotic compound, and the shell covering the core.

Then, to the suspension liquid containing the controlled release particles, as necessary, known additives such as a thickening agent, an antifreezing agent, an antiseptic, a microbial growth inhibitor, and a specific gravity adjuster are blended appropriately.

The thus obtained controlled release particles may be used as is (suspension liquid), that is, may be used as suspension formulation, or for example, may be formulated into a known form such as powder formulation or granular formulation, after solid-liquid separation by filtration and/or centrifugal separation, etc. and used. As necessary, the controlled release particles can be washed with water and/or acid. Furthermore, the suspension liquid can be dried by spraying or by air as is, to be formulated into forms such as powder formulation or granular formulation.

The suspension formulation has a solid content concentration (controlled release particles concentration) of, for example, 1 to 50 mass %, preferably 5 to 40 mass %.

The suspension formulation has an antibiotic compound concentration of, for example, 0.5 to 40 mass %, preferably 1 to 25 mass %.

Meanwhile, powder formulation is excellent in flowability particularly when tribasic calcium phosphate is used as the dispersing agent. By dispersing or suspending the powder formulation in water again, water dispersion formulation or suspension formulation can be prepared again. Thus, the powder formulation is excellent in re-dispersibility in water or forming re-suspension.

Thus, by preparing the controlled release particles as powder formulation at the time of transportation, and preparing (re-formulation, reproduction) the powder formulation again as water dispersion or suspension, the transportation costs can be reduced, and furthermore, its application can be expanded.

The controlled release particles obtained by above-described production method includes a core in which the antibiotic compound is present in the first polymer obtained from the first polymerizable vinyl monomer; and a shell composed of the second polymer and formed to cover the core, and therefore by suppressing the releasing speed of the antibiotic compound, excellent controlled release properties can be achieved, and excellent lasting effects can be exhibited.

By controlled release properties, what is meant is that the encapsulated compound can be released gradually.

When the emulsified liquid contains a silane coupling agent, a silanol group derived from the silane coupling agent is present in the shell, and the silanol group is capable of reacting with inorganic substance (to be specific, metal, metal oxide, etc.) or organic substance (to be specific, cellulose forming paper or lumber, etc.) that forms the base material. Thus, when the controlled release particles are added (blended) to, for example, paint, sealant, or adhesive and used, the controlled release particles are capable of chemically bonding with the above-described base material, and antibiotic properties can be kept for a long period of time.

In the above-described embodiment, although it is described that the second polymerizable vinyl monomer has affinity with water that is higher than that of the first polymerizable vinyl monomer, for example, affinity with water of the second polymerizable vinyl monomer may be substantially the same with that of the first polymerizable vinyl monomer.

That is, the second polymerizable vinyl monomer has affinity with water of substantially the same with affinity with water of the first polymerizable vinyl monomer. To be specific, such a second polymerizable vinyl monomer is hydrophobic.

Examples of such a second polymerizable vinyl monomer include (meth)acrylic acid alkyl ester, and preferably, (meth)acrylic acid alkyl ester having an alkyl moiety with 1 to 3 carbon atoms is used. When the (meth)acrylic acid alkyl ester having an alkyl moiety with 1 to 3 carbon atoms is used singly, as the first polymerizable vinyl monomer, for example, a combination of (meth)acrylic acid alkyl ester having 1 to 3 carbon atoms and (meth)acrylic acid monomer, preferably, a combination of (meth)acrylic acid alkyl ester (to be specific, methyl (meth)acrylate) having one carbon atom and methacrylic acid is selected.

The polar term $\delta_{p,second\ polymer}$ of the second polymer, i.e., a polymer of such a second polymerizable vinyl monomer, is, for example, 5.0 or more to below $6.5[(J/cm^3)^{1/2}]$, preferably 5.5 to $6.5[(J/cm^3)^{1/2}]$, and the hydrogen bonding term $\delta_{h,second\ polymer}$ of the second polymer, the polymer of the second polymerizable vinyl monomer, is, for example, 8.0 $[(J/cm^3)^{1/2}]$ or more and below $13.0[(J/cm^3)^{1/2}]$, preferably 9.0 to $11.0[(J/cm^3)^{1/2}]$.

Thus, the value of $\Delta\delta_{p2}$ deducting the polar term $\delta_{p,first\ polymer}$ of the first polymer from the polar term $\delta_{p,second\ polymer}$ of the second polymer is, for example, $-0.5[(J/cm^3)^{1/2}]$ or more and below $2.0[(J/cm^3)^{1/2}]$, more preferably $-0.2$ to $1.0[(J/cm^3)^{1/2}]$, even more preferably $-0.1$ to $0.0[(J/cm^3)^{1/2}]$.

The value of $\Delta\delta_{h2}$ deducting the hydrogen bonding term $\delta_{h,first\ polymer}$ of the first polymer from the hydrogen bonding term $\delta_{h,second\ polymer}$ of the second polymer is, for example, $-2.0[(J/cm^3)^{1/2}]$ or more and below $2.0[(J/cm^3)^{1/2}]$, more preferably $-0.5$ to $1.0[(J/cm^3)^{1/2}]$, and even more preferably $-0.3$ to $0.0[(J/cm^3)^{1/2}]$.

When the value of $\Delta\delta_{p3}$ and/or $\Delta\delta_{h2}$ are within the above-described range, affinity with water of the second polymer is defined as substantially the same as affinity with water of the first polymer.

In other words, hydrophobicity of the second polymerizable vinyl monomer is substantially the same as hydrophobicity of the first polymerizable vinyl monomer.

Even if affinity with water of the second polymerizable vinyl monomer is substantially the same as affinity with water of the first polymerizable vinyl monomer, the above-described operations and effects can be achieved.

Meanwhile, when affinity with water of the second polymerizable vinyl monomer is higher than that of the first polymerizable vinyl monomer, the antibiotic compound that is not miscible with the shell is preferably used. That is, for the second polymer forming the shell, preferably, the second polymer that is not miscible with the antibiotic compound is used.

To be specific, as shown in the TEM photograph of FIG. 1, the shell (3) is composed of a polymer (second polymer) of a second polymerizable vinyl monomer having higher affinity with water than that of the first polymerizable vinyl monomer. Thus, the shell (3) functions as a barrier layer which prevents the antibiotic compound present in the core (2) from leaking out of the controlled release particles (1).

As a result, controlled release properties of the controlled release particles (1) are improved, and more excellent lasting effects can be exhibited.

EXAMPLES

Details of the abbreviations used in Examples and Comparative Examples are shown below.

OIT: trade name "KATHON 893T" ("KATHON" is registered trademark), 2-n-octyl-4-isothiazoline-3-one, molecular weight 213, melting point: below 20° C., water solubility: 300 ppm, polar term $\delta_{p,compound}$ of solubility parameter $\delta$: 5.47$[(J/cm^3)^{1/2}]$, hydrogen bonding term $\delta_{h,compound}$ of solubility parameter $\delta$: 5.87$[(J/cm^3)^{1/2}]$, manufactured by Rohm and Haas Company IPBC: trade name "Fungitrol 400", 3-iodo-2-propynylbutylcarbamate, molecular weight 281, melting point: 60° C., water solubility: 150 ppm, polar term $\delta_{p,compound}$ of solubility parameter $\delta$: 3.23$[(J/cm^3)^{1/2}]$, hydrogen bonding term $\delta_{h,compound}$ of solubility parameter $\delta$: 7.83 $[(J/cm^3)^{1/2}]$, manufactured by International Specialty Products Inc.

Propiconazole: 1-[2-(2,4-dichlorophenyl)-4-n-propyl-1,3-dioxolane-2-ylmethyl]-1H-1,2,4-triazole, molecular weight 342, melting point: below 20° C., water solubility: 110 ppm, polar term $\delta_{p,compound}$ of solubility parameter $\delta$: 6.55$[(J/cm^3)^{1/2}]$, hydrogen bonding term $\delta_{h,compound}$ of solubility parameter $\delta$: 9.44$[(J/cm^3)^{1/2}]$, manufactured by HAKKO TSUSHO CO., LTD.

Flusilazole: bis(4-fluorophenyl) methyl (1H-1,2,4-triazole-1-ylmethylsliane), molecular weight 315, melting point: 54° C., water solubility: 45 ppm, polar term $\delta_{p,compound}$ of solubility parameter $\delta$: 5.95$[(J/cm^3)^{1/2}]$, hydrogen bonding term $\delta_{h,compound}$ of solubility parameter $\delta$: 6.85$[(J/cm^3)^{1/2}]$, manufactured by ARBROWN CO., LTD.

Prochloraz: N-propyl-N-[2-(2,4,6-trichloro-phenoxy)ethyl] imidazole-1-carboxamide, molecular weight 375, melting point 45 to 52° C., water solubility: 55 ppm, polar term $\delta_{p,compound}$ of solubility parameter $\delta$: 6.87$[(J/cm^3)^{1/2}]$, hydrogen bonding term $\delta_{h,compound}$ of solubility parameter $\delta$: 8.85$[(J/cm^3)^{1/2}]$, manufactured by Maruzen Chemicals Co., Ltd Cyfluthrin: trade name "Preventol HS12" ("Preventol" is registered trademark), (RS)-α-cyano-4-fluoro-3-phenoxy-benzyl=(1RS,3RS)-(1RS,3RS)-3-(2,2-dichlorovinyl)-2,2-methylcyclopropane carboxylate, molecular weight 434, water solubility: 1 to 2 ppb, mixture of isomer I (melting point 57° C.), isomer II (melting point 74° C.), isomer III (melting point 66° C.), and isomer IV (melting point 102° C.), polar term $\delta_{p,compound}$ of solubility parameter $\delta$: 3.46 $[(J/cm^3)^{1/2}]$, hydrogen bonding term $\delta_{h,compound}$ of solubility parameter $\delta$: 6.09 $[(J/cm^3)^{1/2}]$, manufactured by LANXESS Methyl methacrylate: trade name "ACRYESTER M" ("ACRYESTER M" is registered trademark), water solubility: 1.6 mass %, polar term $\delta_{p,monomer\ unit}$ of solubility parameter $\delta$ as monomer unit: 6.69$[(J/cm^3)^{1/2}]$, hydrogen bonding term $\delta_{h,monomer\ unit}$ of solubility parameter $\delta$ as monomer unit: 9.78$[(J/cm^3)^{1/2}]$, manufactured by Mitsubishi Rayon Co., Ltd Isobutyl Methacrylate: water solubility: 0.06 mass %, polar term $\delta_{p,monomer}$ unit of solubility parameter $\delta$ as monomer unit: 3.75$[(J/cm^3)^{1/2}]$, hydrogen bonding term $\delta_{h,monomer\ unit}$ of solubility parameter $\delta$ as monomer unit: 7.32$[(J/cm^3)^{1/2}]$, manufactured by Nippon Shokubai Co., Ltd.

Methacrylic acid: water solubility: 8.9 mass %, polar term $\delta_{p,monomer\ unit}$ of solubility parameter $\delta$ as monomer unit: 7.13$[(J/cm^3)^{1/2}]$, hydrogen bonding term $\delta_{h,monomer\ unit}$ of solubility parameter $\delta$ as monomer unit: 13.03 $[(J/cm^3)^{1/2}]$, manufactured by Mitsubishi Rayon Co., Ltd.

Ethylene glycol dimethacrylate: trade name "Light Ester EG", water solubility: 5.37 ppm, polar term $\delta_{p,monomer\ unit}$ of solubility parameter $\delta$ as monomer unit: 5.37$[(J/cm^3)^{1/2}]$, hydrogen bonding term $\delta_{h,monomer\ unit}$ of solubility parameter $\delta$ as monomer unit: 10.42$[(J/cm^3)^{1/2}]$, manufactured by Kyoeisha Chemical Co., Ltd.

Dilauroyl peroxide: trade name "PEROYL® L" ("PEROYL" is registered trademark), manufactured by NOF CORPORATION TCP-10U: trade name, a suspension liquid of 10% tribasic calcium phosphate $[Ca_3(PO_4)_2]$. $Ca(OH)_2$, manufactured by Matsuo Yakuhin Sangyo K. K.

PLYSURF A210G: trade name, "PLYSURF" is registered trademark, polyoxyethylene phosphate, non-ionic surfactant, manufactured by DAI-ICHI KOGYO SEIYAKU CO., LTD.

2-hydroxyethyl methacrylate: hydrophilic (miscible with water), polar term $\delta_{p,monomer\ unit}$ of solubility parameter $\delta$ as monomer unit: 7.48$[(J/cm^3)^{1/2}]$, hydrogen bonding term $\delta_{h,monomer\ unit}$ of solubility parameter $\delta$ as monomer unit: 16.98$[(J/cm^3)^{1/2}]$, manufactured by Nippon Shokubai Co., Ltd.

Pelex OT-P: trade name, "Pelex" is registered trademark, sodium dialkyl sulfosuccinic acid, manufactured by Kao Corporation

Example 1

Formulation of Suspension Containing OIT-Containing Controlled Release Particles (First Step: Suspension Polymerization, Second Step: Suspension Polymerization)

A200 mL beaker (1) was charged with 60.0 g of OIT, 30.0 g of methyl methacrylate, 5.0 g of methacrylic acid, 5.0 g of ethylene glycol dimethacrylate, and 1.9 g of dilauroyl peroxide, and then the mixture was stirred at room temperature, thereby preparing a homogeneous hydrophobic solution.

Separately, a 1000 mL beaker (2) was charged with 120.0 g of ion-exchange water, 120.0 g of TCP-10U, and 1.0 g of a solution of 5% PLYSURF A210G in water, and then the mixture was stirred at room temperature, thereby producing a homogeneous suspension liquid.

Then, the hydrophobic solution was added to the 1000 mL beaker (2), and the mixture was stirred with T.K. Homo Mixer MARK Model 2.5 (manufactured by PRIMIX Corporation) at a number of revolution of 5000 rpm for 5 min, thereby suspending the hydrophobic solution, and preparing a suspension liquid.

Thereafter, the suspension liquid was transferred to a 500 mL, 4-neck flask equipped with a stirrer, a reflux condenser, a thermometer, and a nitrogen inlet tube, and subjected to suspension polymerization under nitrogen gas current, while stirring and increasing the temperature (first step).

The suspension polymerization was started when the temperature of the suspension liquid reached 65° C. while the temperature of the suspension liquid was increasing, and then subsequently, the temperature of the suspension liquid was kept at 70° C. for 2 hours.

Thereafter, the suspension liquid was cooled to room temperature.

Separately, a 200 mL beaker (3) was charged with 17.2 g of ion-exchange water and 22.8 g of a solution of 1% Pelex OT-P in water, and then the mixture was stirred at room temperature, thereby preparing a homogenous aqueous solution.

Then, 40.0 g of methyl methacrylate was added to the 200 mL beaker (3), and the mixture was stirred with T.K. Homo Mixer MARK Model 2.5 (manufactured by PRIMIX Corporation) at a number of revolution of 10000 rpm for 10 min, thereby emulsifying methyl methacrylate, and preparing an emulsified liquid.

Then, the emulsified liquid was added to the suspension liquid while stirring the suspension liquid cooled to room temperature after the reaction, and the mixture was stirred for 2 hours.

Thereafter, under nitrogen gas current, the temperature of the mixture was increased while stirring, allowing suspension polymerization (second step).

The suspension polymerization was started when the temperature of the suspension liquid reached 65° C. while the temperature of the suspension liquid was increasing, and then subsequently, the temperature of the suspension liquid was kept at 70° C. for 3 hours.

Thereafter, the suspension liquid was cooled to room temperature.

A suspension liquid (suspension formulation) of controlled release particles including a core containing OIT and a shell covering the core was obtained in this manner.

Example 2

Formulation of Suspension Containing OIT-Containing Controlled Release Particles (First Step: Suspension Polymerization, Second Step: Suspension Polymerization)

A suspension liquid (suspension formulation) of controlled release particles including a core containing OIT and a shell covering the core was obtained in the same manner as in Example 1, except that 30.0 g of methyl methacrylate in the hydrophobic solution was changed to 30.0 g of isobutyl methacrylate.

Example 3

Formulation of Suspension Containing OIT-Containing Controlled Release Particles (First Step: Suspension Polymerization, Second Step: Suspension Polymerization)

A suspension liquid (suspension formulation) of controlled release particles including a core containing OIT and a shell covering the core was obtained in the same manner as in Example 1, except that 30.0 g of methyl methacrylate in the hydrophobic solution was changed to 30.0 g of isobutyl methacrylate, and the 200 mL beaker (3) was charged with 20.0 g of methyl methacrylate and 20.0 g of 2-hydroxyethyl methacrylate instead of 40.0 g of methyl methacrylate to be emulsified.

Example 4

Formulation of Suspension Containing OIT-Containing Controlled Release Particles (First Step: Suspension Polymerization, Second Step: Suspension Polymerization)

A suspension liquid (suspension formulation) of controlled release particles including a core containing OIT and a shell covering the core was obtained in the same manner as in Example 1, except that 30.0 g of methyl methacrylate in the hydrophobic solution was changed to 30.0 g of isobutyl methacrylate, and the 200 mL beaker (3) was charged with 40.0 g of 2-hydroxyethyl methacrylate instead of 40.0 g of methyl methacrylate to be emulsified.

Example 5

Formulation of Suspension Containing IPBC-Containing Controlled Release Particles (First Step: Suspension Polymerization, Second Step: Suspension Polymerization)

A suspension liquid (suspension formulation) of controlled release particles including a core containing IPBC and a shell covering the core was produced in the same manner as in Example 1, except that 60.0 g of OIT in the hydrophobic solution was changed to 25.0 g of IPBC, and 30.0 g of methyl methacrylate was changed to 65.0 g of isobutyl methacrylate.

Example 6

Formulation of Suspension Containing IPBC-Containing Controlled Release Particles (First Step: Suspension Polymerization, Second Step: Suspension Polymerization)

A suspension liquid (suspension formulation) of controlled release particles including a core containing IPBC and a shell covering the core was produced in the same manner as in Example 1, except that 60.0 g of OIT in the hydrophobic solution was changed to 25.0 g of IPBC, 30.0 g of methyl methacrylate was changed to 65.0 g of isobutyl methacrylate, and the 200 mL beaker (3) was charged with 40.0 g of 2-hydroxyethyl methacrylate instead of 40.0 g of methyl methacrylate to be emulsified.

Example 7

Formulation of Suspension Containing Propiconazole-Containing Controlled Release Particles (First Step: Suspension Polymerization, Second Step: Suspension Polymerization)

A suspension liquid (suspension formulation) of controlled release particles including a core containing Propiconazole and a shell covering the core was produced in the same manner as in Example 1, except that 60.0 g of OIT in the hydrophobic solution was changed to 25.0 g of Propiconazole, and 30.0 g of methyl methacrylate was changed to 65.0 g of isobutyl methacrylate.

Example 8

Formulation of Suspension Containing Propiconazole-Containing Controlled Release Particles (First Step: Suspension Polymerization, Second Step: Suspension Polymerization)

A suspension liquid (suspension formulation) of controlled release particles including a core containing Propiconazole and a shell covering the core was produced in the same manner as in Example 1, except that 60.0 g of OIT in the hydrophobic solution was changed to 25.0 g of Propiconazole, and 30.0 g of methyl methacrylate was changed to 65.0 g of isobutyl methacrylate, and the 200 mL beaker (3) was charged with 40.0 g of 2-hydroxyethyl methacrylate instead of 40.0 g of methyl methacrylate to be emulsified.

Example 9

Formulation of Suspension Containing Flusilazole-Containing Controlled Release Particles (First Step: Suspension Polymerization, Second Step: Suspension Polymerization)

A suspension liquid (suspension formulation) of controlled release particles including a core containing Flusilazole and a shell covering the core was produced in the same manner as in Example 1, except that 60.0 g of OIT in the hydrophobic solution was changed to 25.0 g of Flusilazole, and 30.0 g of methyl methacrylate was changed to 65.0 g of isobutyl methacrylate.

Example 10

Formulation of Suspension Containing Flusilazole-Containing Controlled Release Particles (First Step: Suspension Polymerization, Second Step: Suspension Polymerization)

A suspension liquid (suspension formulation) of controlled release particles including a core containing Flusilazole and a shell covering the core was produced in the same manner as in Example 1, except that 60.0 g of OIT in the hydrophobic solution was changed to 25.0 g of Flusilazole, and 30.0 g of methyl methacrylate was changed to 65.0 g of isobutyl methacrylate, and the 200 mL beaker (3) was charged with 40.0 g of 2-hydroxyethyl methacrylate instead of 40.0 g of methyl methacrylate to be emulsified.

Example 11

Formulation of Suspension Containing Prochloraz-Containing Controlled Release Particles (First Step: suspension polymerization, Second Step: suspension polymerization)

A suspension liquid (suspension formulation) of controlled release particles including a core containing prochloraz and a shell covering the core was produced in the same manner as in Example 1, except that 60.0 g of OIT in the hydrophobic solution was changed to 25.0 g of prochloraz, and 30.0 g of methyl methacrylate was changed to 65.0 g of isobutyl methacrylate.

Example 12

Formulation of Suspension Containing Prochloraz-Containing Controlled Release Particles (First Step: Suspension Polymerization, Second Step: Suspension Polymerization)

A suspension liquid (suspension formulation) of controlled release particles including a core containing prochloraz and a shell covering the core was produced in the same manner as in Example 1, except that 60.0 g of OIT in the hydrophobic solution was changed to 25.0 g of prochloraz, and 30.0 g of methyl methacrylate was changed to 65.0 g of isobutyl methacrylate, and the 200 mL beaker (3) was charged with 40.0 g of 2-hydroxyethyl methacrylate instead of 40.0 g of methyl methacrylate to be emulsified.

Example 13

Formulation of Suspension Containing Cyfluthrin-Containing Controlled Release Particles (First Step: Suspension Polymerization, Second Step: Suspension Polymerization)

A suspension liquid (suspension formulation) of controlled release particles including a core containing cyfluthrin and a shell covering the core was produced in the same manner as in Example 1, except that 60.0 g of OIT in the hydrophobic solution was changed to 25.0 g of cyfluthrin, and 30.0 g of methyl methacrylate was changed to 65.0 g of isobutyl methacrylate.

Example 14

Formulation of Suspension Containing Cyfluthrin-Containing Controlled Release Particles (First Step: Suspension Polymerization, Second Step: Suspension Polymerization)

A suspension liquid (suspension formulation) of controlled release particles including a core containing cyfluthrin and a shell covering the core was produced in the same manner as in Example 1, except that 60.0 g of OIT in the hydrophobic solution was changed to 25.0 g of prochloraz, and 30.0 g of methyl methacrylate was changed to 65.0 g of isobutyl methacrylate, and the 200 mL beaker (3) was charged with 40.0 g of 2-hydroxyethyl methacrylate instead of 40.0 g of methyl methacrylate to be emulsified.

Comparative Example 1

Formulation of Suspension Containing OIT-Containing Controlled Release Particles (First Step: Suspension Polymerization)

A 200 mL beaker (1) was charged with 60.0 g of OIT, 30.0 g of methyl methacrylate, 5 g of methacrylic acid, 5.0 g of ethylene glycol dimethacrylate, and 1.9 g of dilauroyl peroxide, and then the mixture was stirred at room temperature, thereby preparing a homogenous hydrophobic solution.

Separately, a 1000 mL beaker (2) was charged with 120.0 g of ion-exchange water, 120.0 g of TCP-10U, and 1.0 g of a solution of 5% PLYSURF A210G in water, and then the mixture was stirred at room temperature, thereby producing a homogenous suspension liquid.

Then, the hydrophobic solution was added to the 1000 mL beaker (2), and the mixture was stirred with T.K. Homo Mixer MARK Model 2.5 (manufactured by PRIMIX Corporation) at a number of revolution of 5000 rpm for 5 min, thereby dispersing the hydrophobic solution, and preparing a suspension liquid.

Thereafter, the suspension liquid was transferred to a 500 mL, 4-neck flask equipped with a stirrer, a reflux condenser, a thermometer, and a nitrogen inlet tube, and subjected to suspension polymerization under nitrogen gas current, while stirring and increasing the temperature (first step).

The suspension polymerization was started when the temperature of the suspension liquid reached 65° C. while the temperature of the suspension liquid was increasing, and then subsequently, the temperature of the suspension liquid was kept at 70° C. for 2 hours.

Thereafter, the suspension liquid was cooled to room temperature.

A suspension liquid (suspension formulation) of controlled release particles containing OIT was obtained in this manner.

Comparative Example 2

Formulation of Suspension Containing OIT-Containing Controlled Release Particles (First Step: Suspension Polymerization)

A suspension liquid (suspension formulation) of controlled release particles containing OIT was produced in the same manner as in Comparative Example 1, except that 30.0 g of methyl methacrylate in the hydrophobic solution was changed to 30.0 g of isobutyl methacrylate.

Comparative Example 3

Formulation of Suspension Containing IPBC-Containing Controlled Release Particles (First Step: Suspension Polymerization)

A suspension liquid (suspension formulation) of controlled release particles containing IPBC was produced in the same manner as in Comparative Example 1, except that 60.0 g of OIT in the hydrophobic solution was changed to 25.0 g of IPBC, and 30.0 g of methyl methacrylate was changed to 65.0 g of isobutyl methacrylate.

Comparative Example 4

Formulation of Suspension Containing Propiconazole-Containing Controlled Release Particles (First Step: Suspension Polymerization)

A suspension liquid (suspension formulation) of controlled release particles containing Propiconazole was pro duced in the same manner as in Comparative Example 1, except that 60.0 g or OIT in the hydrophobic solution was changed to 25.0 g of Propiconazole, and 30.0 g of methyl methacrylate was changed to 65.0 g of isobutyl methacrylate.

Comparative Example 5

Formulation of Suspension Containing Flusilazole-Containing Controlled Release Particles (First Step: Suspension Polymerization)

A suspension liquid (suspension formulation) of controlled release particles containing Flusilazole was produced in the same manner as in Comparative Example 1, except that 60.0 g of OIT in the hydrophobic solution was changed to 25.0 g of Flusilazole, and 30.0 g of methyl methacrylate was changed to 65.0 g of isobutyl methacrylate.

Comparative Example 6

Formulation of Suspension Containing Prochloraz-Containing Controlled Release Particles (First Step: Suspension Polymerization)

A suspension liquid (suspension formulation) of controlled release particles containing prochloraz was produced in the same manner as in Comparative Example 1, except that 60.0 g of OIT in the hydrophobic solution was changed to 25.0 g of prochloraz, and 30.0 g of methyl methacrylate was changed to 65.0 g of isobutyl methacrylate.

Comparative Example 7

Formulation of Suspension Containing Cyfluthrin-Containing Controlled Release Particles (First Step: Suspension Polymerization)

A suspension liquid (suspension formulation) of controlled release particles containing cyfluthrin was produced in the same manner as in Comparative Example 1, except that 60.0 g of OIT in the hydrophobic solution was changed to 25.0 g of cyfluthrin, and 30.0 g of methyl methacrylate was changed to 65.0 g of isobutyl methacrylate.

(Mixing Formulation)

Formulation of components in Examples and Comparative Examples is shown in Table 2 to Table 4. In the tables, values of the mixing formulation are shown in grams.

TABLE 2

| | | | Examples | | | | | | |
|---|---|---|---|---|---|---|---|---|---|
| | | | Example 1 | Example 2 | Example 3 | Example 4 | Example 5 | Example 6 | Example 7 |
| Hydrophobic Solution | Core Ingredient Component | Antibiotic Compound | OIT | 60.0 | 60.0 | 60.0 | 60.0 | — | — | — |
| | | | IPBC | — | — | — | — | 25.0 | 25.0 | — |
| | | | Propiconazole | — | — | — | — | — | — | 25.0 |
| | | | Flusilazole | — | — | — | — | — | — | — |
| | | | Prochloraz | — | — | — | — | — | — | — |
| | | | Cyfluthrin | — | — | — | — | — | — | — |
| | | First Polymerizable Vinyl Monomer | Miscible Monomer Methyl Methacrylate | 30.0 | — | — | — | — | — | — |
| | | | Isobutyl Methacrylate | — | 30.0 | 30.0 | 30.0 | 65.0 | 65.0 | 65.0 |
| | | | Methacrylic Acid | 5.0 | 5.0 | 5.0 | 5.0 | 5.0 | 5.0 | 5.0 |
| | | Crosslinkable Monomer | Ethylene Glycol Dimethacrylate | 5.0 | 5.0 | 5.0 | 5.0 | 5.0 | 5.0 | 5.0 |
| | Initiator | | Dilauroyl Peroxide | 1.9 | 1.9 | 1.9 | 1.9 | 1.9 | 1.9 | 1.9 |
| | Ion-exchange water | | | 120.0 | 120.0 | 120.0 | 120.0 | 120.0 | 120.0 | 120.0 |
| Dispersing Agent | | | SOLUTION OF 5% PLYSURF A210G IN WATER | 120.0 | 120.0 | 120.0 | 120.0 | 120.0 | 120.0 | 120.0 |
| Surfactant | | | TCP-10U | 1.0 | 1.0 | 1.0 | 1.0 | 1.0 | 1.0 | 1.0 |
| Emulsified Liquid | Second Polymerizable Vinyl Monomer | | Methyl Methacrylate | 40.0 | 40.0 | 20.0 | — | 40.0 | 40.0 | 40.0 |
| | | | 2-hydroxyethyl methacrylate | — | — | 20.0 | 40.0 | — | — | — |
| | Emulsifier | | Solution of 1% Pelex OT-P in Water | 22.8 | 22.8 | 22.8 | 22.8 | 22.8 | 22.8 | 22.8 |
| | Ion-exchange water | | | 17.2 | 17.2 | 17.2 | 17.2 | 17.2 | 17.2 | 17.2 |
| Solubility Parameter $\delta$ [(J/cm$^3$)$^{1/2}$] | Core | Antibiotic Compound | $\delta_{p,compound}$ | 5.47 | 5.47 | 5.47 | 5.47 | 3.23 | 3.23 | 6.55 |
| | | | $\delta_{h,compound}$ | 5.87 | 5.87 | 5.87 | 5.87 | 7.83 | 7.83 | 9.44 |
| | | First Polymer | $\delta_{p,first\ polymer}$ | 6.07 | 4.38 | 4.38 | 4.38 | 4.38 | 4.38 | 4.38 |
| | | | $\delta_{h,first\ polymer}$ | 9.52 | 8.42 | 8.42 | 8.42 | 8.42 | 8.42 | 8.42 |
| | Shell | Second Polymer | $\delta_{p,second\ polymer}$ | 5.98 | 5.98 | 6.73 | 7.48 | 5.98 | 7.48 | 5.98 |
| | | | $\delta_{h,second\ polymer}$ | 9.25 | 9.25 | 13.11 | 16.98 | 9.25 | 16.98 | 9.25 |
| | $\Delta\delta_{p1}$ ($=\delta_{p,first\ polymer}-\delta_{p,compound}$)[(J/cm$^3$)$^{1/2}$] | | | 0.60 | -1.09 | -1.09 | -1.09 | 1.15 | 1.15 | -2.17 |
| | $\Delta\delta_{h1}$ ($=\delta_{h,first\ polymer}-\delta_{h,compound}$)[(J/cm$^3$)$^{1/2}$] | | | 3.65 | 2.55 | 2.55 | 2.55 | 0.59 | 0.59 | -1.02 |
| | $\Delta\delta_{p2}$ ($=\delta_{p,second\ polymer}-\delta_{p,first\ polymer}$)[(J/cm$^3$)$^{1/2}$] | | | -0.09 | 1.60 | 2.35 | 3.10 | 1.60 | 3.10 | 1.60 |
| | $\Delta\delta_{h2}$ ($=\delta_{h,second\ polymer}-\delta_{h,first\ polymer}$)[(J/cm$^3$)$^{1/2}$] | | | -0.27 | 0.83 | 4.69 | 8.56 | 0.83 | 8.56 | 0.83 |
| Evaluation | Controlled Release Properties Test | Remaining Rate (%) | | 29 | 30 | 37 | 40 | 26 | 38 | — |
| | | Controlled-release Rate (%) | | — | — | — | — | — | — | 12 |

TABLE 3

| | | | Examples | | | | | | | |
|---|---|---|---|---|---|---|---|---|---|---|
| | | | Example 8 | Example 9 | Example 10 | Example 11 | Example 12 | Example 13 | Example 14 |
| Hydrophobic Solution | Core Ingredient Component | Antibiotic Compound | OIT | — | — | — | — | — | — | — |
| | | | IPBC | — | — | — | — | — | — | — |
| | | | Propiconazole | 25.0 | — | — | — | — | — | — |
| | | | Flusilazole | — | 25.0 | — | — | — | — | — |
| | | | Prochloraz | — | — | 25.0 | 25.0 | 25.0 | 25.0 | 25.0 |
| | | | Cyfluthrin | — | — | — | — | — | — | — |
| | First Polymerizable Vinyl Monomer | Miscible Monomer | Methyl Methacrylate | 65.0 | 65.0 | 65.0 | 65.0 | 65.0 | 65.0 | 65.0 |
| | | | Isobutyl Methacrylate | 5.0 | 5.0 | 5.0 | 5.0 | 5.0 | 5.0 | 5.0 |
| | | | Methacrylic Acid | 5.0 | 5.0 | 5.0 | 5.0 | 5.0 | 5.0 | 5.0 |
| | | Crosslinkable Monomer | Ethylene Glycol Dimethacrylate | — | — | — | — | — | — | — |
| | Initiator | | Dilauroyl Peroxide | 1.9 | 1.9 | 1.9 | 1.9 | 1.9 | 1.9 | 1.9 |
| | Ion-exchange water | | | 120.0 | 120.0 | 120.0 | 120.0 | 120.0 | 120.0 | 120.0 |
| Dispersing Agent | | | TCP-10U | 120.0 | 120.0 | 120.0 | 120.0 | 120.0 | 120.0 | 120.0 |
| Surfactant | | | SOLUTION OF 5% PLYSURF A210G IN WATER | 1.0 | 1.0 | 1.0 | 1.0 | 1.0 | 1.0 | 1.0 |
| Emulsified Liquid | Second Polymerizable Vinyl Monomer | | Methyl Methacrylate | 40.0 | 40.0 | 40.0 | 40.0 | 40.0 | 40.0 | 40.0 |
| | | | 2-hydroxyethyl methacrylate | — | — | — | — | — | — | — |
| | Emulsifier | | Solution of 1% Pelex OT-P in Water | — | — | — | — | — | — | — |
| | Ion-exchange water | | | — | — | — | — | — | — | — |
| Solubility Parameter δ [(J/cm³)^{1/2}] | Antibiotic Compound | | $\delta_{p,compound}$ | 22.8 | 22.8 | 22.8 | 22.8 | 22.8 | 22.8 | 22.8 |
| | | | $\delta_{h,compound}$ | 17.2 | 17.2 | 17.2 | 17.2 | 17.2 | 17.2 | 17.2 |
| | First Polymer | | $\delta_{p,first\ polymer}$ | 6.55 | 5.95 | 5.95 | 6.87 | 6.87 | 3.46 | 3.46 |
| | | | $\delta_{h,first\ polymer}$ | 9.44 | 6.85 | 6.85 | 8.85 | 8.85 | 6.09 | 6.09 |
| | Second Polymer | | $\delta_{p,second\ polymer}$ | 4.38 | 4.38 | 4.38 | 4.38 | 4.38 | 4.38 | 4.38 |
| | | | $\delta_{h,second\ polymer}$ | 8.42 | 8.42 | 8.42 | 8.42 | 8.42 | 8.42 | 8.42 |
| | $\Delta\delta_{p1}$ ($=\delta_{p,first\ polymer}-\delta_{p,compound}$)[(J/cm³)^{1/2}] | | | 7.48 | 5.98 | 7.48 | 5.98 | 7.48 | 5.98 | 7.48 |
| | $\Delta\delta_{h1}$ ($=\delta_{h,first\ polymer}-\delta_{h,compound}$)[(J/cm³)^{1/2}] | | | 16.98 | 9.25 | 16.98 | 9.25 | 16.98 | 9.25 | 16.98 |
| | $\Delta\delta_{p2}$ ($=\delta_{p,second\ polymer}-\delta_{p,first\ polymer}$)[(J/cm³)^{1/2}] | | | −2.17 | −1.57 | −1.57 | −2.49 | −2.49 | 0.92 | 0.92 |
| | $\Delta\delta_{h2}$ ($=\delta_{h,second\ polymer}-\delta_{h,first\ polymer}$)[(J/cm³)^{1/2}] | | | −1.02 | 1.57 | 1.57 | −0.43 | −0.43 | 2.33 | 2.33 |
| | | | | 3.10 | 1.60 | 3.10 | 1.60 | 3.10 | 1.60 | 3.10 |
| | | | | 8.56 | 0.83 | 8.56 | 0.83 | 8.56 | 0.83 | 8.56 |
| Evaluation | Controlled Release Properties Test | | Remaining Rate (%) | 32 | 3 | 11 | 3 | 8 | 5 | 9 |
| | | | Controlled-release Rate (%) | — | — | — | — | — | — | — |

TABLE 4

| | | | Comparative Examples | | | | | | |
|---|---|---|---|---|---|---|---|---|---|
| | | | Comp. Ex. 1 | Comp. Ex. 2 | Comp. Ex. 3 | Comp. Ex. 4 | Comp. Ex. 5 | Comp. Ex. 6 | Comp. Ex. 7 |
| Hydrophobic Solution | Core Ingredient Component | Antibiotic Compound | OIT | 60.0 | 60.0 | — | — | — | — | — |
| | | | IPBC | — | — | 25.0 | — | — | — | — |
| | | | Propiconazole | — | — | — | 25.0 | — | — | — |
| | | | Flusilazole | — | — | — | — | 25.0 | — | — |
| | | | Prochloraz | — | — | — | — | — | 25.0 | — |
| | | | Cyfluthrin | — | — | — | — | — | — | 25.0 |
| | | First Polymerizable Vinyl Monomer | Miscible Monomer | Methyl Methacrylate | 30.0 | — | — | — | — | — | — |
| | | | | Isobutyl Methacrylate | — | 30.0 | 65.0 | 65.0 | 65.0 | 65.0 | 65.0 |
| | | | | Methacrylic Acid | 5.0 | 5.0 | 5.0 | 5.0 | 5.0 | 5.0 | 5.0 |
| | | | Crosslinkable Monomer | Ethylene Glycol Dimethacrylate | 5.0 | 5.0 | 5.0 | 5.0 | 5.0 | 5.0 | 5.0 |
| | Initiator | | Dilauroyl Peroxide | 1.9 | 1.9 | 1.9 | 1.9 | 1.9 | 1.9 | 1.9 |
| | Ion-exchange water | | | 120.0 | 120.0 | 120.0 | 120.0 | 120.0 | 120.0 | 120.0 |
| Dispersing Agent | | | TCP-10U | 120.0 | 120.0 | 120.0 | 120.0 | 120.0 | 120.0 | 120.0 |
| Surfactant | | | SOLUTION OF 5% PLYSURF A210G IN WATER | 1.0 | 1.0 | 1.0 | 1.0 | 1.0 | 1.0 | 1.0 |
| Emulsified Liquid | Second Polymerizable Vinyl | | Methyl Methacrylate | — | — | — | — | — | — | — |
| | | | 2-hydroxyethyl methacrylate | — | — | — | — | — | — | — |
| | Emulsifier | | Solution of 1% Pelex OT-P in Water | — | — | — | — | — | — | — |
| | | | Ion-exchange water | — | — | — | — | — | — | — |
| Solubility Parameter δ [(J/cm³)^{1/2}] | Core | Antibiotic Compound | $\delta_{p,compound}$ | 5.47 | 5.47 | 3.23 | 6.55 | 5.95 | 6.87 | 3.46 |
| | | | $\delta_{h,compound}$ | 5.87 | 5.87 | 7.83 | 9.44 | 6.85 | 8.85 | 6.09 |
| | | First Polymer | $\delta_{p,first\ polymer}$ | 6.07 | 4.38 | 4.38 | 4.38 | 4.38 | 4.38 | 4.38 |
| | | | $\delta_{h,first\ polymer}$ | 9.52 | 8.42 | 8.42 | 8.42 | 8.42 | 8.42 | 8.42 |
| | Shell | Second Polymer | $\delta_{p,second\ polymer}$ | — | — | — | — | — | — | — |
| | | | $\delta_{h,second\ polymer}$ | — | — | — | — | — | — | — |
| | Δ$\delta_{p1}$ (= $\delta_{p,first\ polymer} - \delta_{p,compound}$)[(J/cm³)^{1/2}] | | | 0.60 | −1.09 | 1.15 | −2.17 | −1.57 | −2.49 | 0.92 |
| | Δ$\delta_{h1}$ (= $\delta_{h,first\ polymer} - \delta_{h,compound}$)[(J/cm³)^{1/2}] | | | 3.65 | 2.55 | 0.59 | −1.02 | 1.57 | −0.43 | 2.33 |
| | Δ$\delta_{p2}$ (= $\delta_{p,second\ polymer} - \delta_{p,first\ polymer}$)[(J/cm³)^{1/2}] | | | — | — | — | — | — | — | — |
| | Δ$\delta_{h2}$ (= $\delta_{h,second\ polymer} - \delta_{h,first\ polymer}$)[(J/cm³)^{1/2}] | | | — | — | — | — | — | — | — |
| Evaluation | Controlled Release Properties Test | | Remaining Rate (%) | — | 13 | 65 | 57 | 23 | 14 | 15 |
| | | | Controlled-release Rate (%) | — | — | — | — | — | — | — |

Evaluation
(Calculation of Solubility Parameter δ)
1. The polar term $\delta_{p,\text{first polymer}}$ and the hydrogen bonding term $\delta_{h,\text{first polymer}}$ of the solubility parameter δ of the first polymer, and the polar term $\delta_{p,\text{second polymer}}$ and the hydrogen bonding term $\delta_{h,\text{second polymer}}$ of the solubility parameter δ of the second polymer were calculated as described above.

Table 2 to Table 4 show the results of calculation along with the polar term $\delta_{p,\text{compound}}$ and the hydrogen bonding term $\delta_{h,\text{compound}}$ of the solubility parameter δ of the antibiotic compound (ref: Table 1).

2. $\Delta\delta_{h1}(=\delta_{h,\text{first polymer}}-\delta_{h,\text{compound}})$, $\delta_{p1}(=\delta_{p,\text{first polymer}}-\delta_{p,\text{compound}})$, $\Delta\delta_{p2}(=\delta_{p,\text{second polymer}}-\delta_{p,\text{first polymer}})$ and $\Delta\delta_{h2}(=\delta_{h,\text{second polymer}}-\delta_{h,\text{first polymer}})$ were calculated.

The results are shown in Table 2 to Table 4.

Evaluation

1. TEM (Transmission Electron Microscope) Observation

The suspension liquid (suspension) of Example 4 was freeze-dried, then dispersed in a bisphenol liquid epoxy resin, and thereafter cured with amine. Then, the cured product was cut with an ultramicrotome to expose its cross section; the cross section was dyed with osmium tetroxide, and as necessary, also with ruthenium tetroxide; the cross section was cut out with an ultramicrotome into extremely thin slices, thereby preparing samples. The prepared samples were observed with a transmission electron microscope (model number "H-7100", manufactured by Hitachi, Ltd.). FIG. 1 shows an image-processed TEM photograph of Example 4.

2. Controlled Release Properties Test (1) Controlled Release Properties Test of OIT-Containing Controlled Release Particles (Examples 1 to 4 and Comparative Example 2)

Controlled release properties test was conducted for the OIT-containing controlled release particles of Examples 1 to 4 and Comparative Example 2 in the following manner.

The suspension liquids (suspension formulation) of controlled release particles obtained in Examples 1 to 4 and Comparative Example 2 were added to a commercially available acrylic styrene emulsion while stirring so that the OIT concentration was 0.15 mass %, and the mixture was stiffed for 1 hour.

Then, the above-described acrylic styrene emulsion was applied on an aluminum plate (JIS A 1050P, 20 cm×20 cm) using a bar coater, thereby forming a coating.

The coating was dried at 40° C. for 24 hours, thereby producing a controlled release particles-containing film, and thereafter, the controlled release particles-containing film was cut into a size of 7 cm×15 cm, thereby producing test pieces. The test pieces were attached to Dewpanel Weather Meter, and exposed to continuous rainfall for 2 weeks.

Thereafter, the exposed test pieces were cut into a size of 2.5 cm×2.5 cm, 10 mL of methanol was added thereto, and OIT was extracted using an ultrasonic washer for 30 minutes.

The above-described processes were conducted also for unexposed test pieces.

The OTT amount extracted as described above was measured using HPLC, and the remaining rate of OIT of controlled release particles in controlled release particles-containing film was calculated from the unexposed test pieces and exposed test pieces.

The results are shown in Tables 2 and 4

(2) Controlled Release Properties Test (Examples 5 to 12 and Comparative Examples 3 to 6) on IPBC-Containing Controlled Release Particles, Propiconazole-Containing Controlled Release Particles, Flusilazole-Containing Controlled Release Particles, and Prochloraz-Containing Controlled Release Particles The controlled release properties test was conducted for the controlled release particles in the following manner.

First, a suspension liquid of controlled release particles was prepared such that the antibiotic compound content of the controlled release particles of each of Examples 5 to 12 and Comparative Examples 3 to 6 was 100 mg.

Then, a cylindrical filter paper (Toyo Roshi Kaisha, Ltd. No. 84, external diameter×internal diameter×height=28× 25×100 mm) was cut transversely, thereby preparing a cylindrical filter paper with a height of 30 mm.

Then, the prepared suspension liquids were slowly poured individually onto the filter papers, and thereafter dried in air.

To the filter paper, water in an amount of 900 mL was passed through using a metered-dose tube pump at a flow rate of 20 mL/hr, and controlled-release rate of the antibiotic compound was calculated using HPLC based on the antibiotic compound amount of the obtained filtrate. The results are shown in Table 2 to Table 4.

(3) Controlled Release Properties Test of Cyfluthrin-Containing Controlled Release Particles (Examples 13, 14, and Comparative Example 7)

Controlled release properties test was conducted for cyfluthrin-containing controlled release particles of Examples 13, 14, and Comparative Example 7 in the following manner.

First, 1 g of a suspension liquid of controlled release particles containing 100 mg of cyfluthrin was prepared for each of controlled release particles of Examples 13 to 14 and Comparative Example 7.

Then, two sheets of circular filter paper (Toyo Roshi Kaisha, Ltd. No. 5C, corresponds to type 5C of JIS P 3801) were piled and folded to be pleated.

Then, to the filter paper, the prepared suspension liquids were poured slowly, and thereafter dried in air.

Thereafter, the filter paper was put into a glass bottle, and 100 mL of ion-exchange water/methanol (=50/50 (volume ratio)) mixture liquid was added thereto, and allowed to stand and to be impregnated at room temperature for 24 hours. Then, the ion-exchange water/methanol mixture was collected, 100 mL of another ion-exchange water/methanol mixture liquid was added thereto, and allowed to stand and to be impregnated for 24 hours at room temperature. Thereafter, the above-described ion-exchange water/methanol mixture liquid exchange operation was repeated three times.

The controlled-release rate of the cyfluthrin was calculated using GC based on the ion-exchange water/methanol mixture liquid collected for the third time. The results are shown in Tables 3 and 4.

While the illustrative embodiments of the present invention are provided in the above description, such is for illustrative purpose only and it is not to be construed as limiting the scope of the present invention. Modification and variation of the present invention that will be obvious to those skilled in the art is to be covered by the following claims.

INDUSTRIAL APPLICABILITY

Controlled release particles of the present invention can be applied (or blended) to various industrial products, for example, can be blended in indoor/outdoor paint, rubber, fiber, resin, plastic, adhesive, joint mixture, sealing agent, building material, caulking agent, soil treating agent, lumber, white water in paper-making processes, pigment, treatment liquid for printing plates, cooling water, ink, cutting oil, cosmetic products, nonwoven fabric, spinning oil, leather; and allows controlled-release of the antibiotic compound that is contained to exhibit lasting effects of the antibiotic compound.

The invention claimed is:

1. A controlled release particle consisting of:
    a core
        formed by suspension polymerization of a core ingredient component containing an antibiotic compound and a first polymerizable vinyl monomer, the core ingredient component being prepared in the absence of a solvent and thus the core ingredient component is solvent-free and
        containing a first polymer of the first polymerizable vinyl monomer, and the antibiotic compound present in the first polymer; and
    a shell
        formed by suspension polymerization of a second polymerizable vinyl monomer having affinity with water of the same or higher than that of the first polymerizable vinyl monomer,
        containing a second polymer obtained from the second polymerizable vinyl monomer, and
        covering the core,
    wherein the antibiotic compound is dispersed in a matrix composed of the first polymer in the core.

* * * * *